United States Patent [19]

Lopez-Berestein et al.

[11] Patent Number: 5,032,404
[45] Date of Patent: Jul. 16, 1991

[54] LIPSOME-INCORPORATION OF POLYENES

[75] Inventors: Gabriel Lopez-Berestein; Reeta Mehta, both of Houston, Tex.

[73] Assignee: Board of Regents, The University of Texas System, Austin, Tex.

[21] Appl. No.: 314,710

[22] Filed: Feb. 23, 1989

[51] Int. Cl.$^5$ .............................................. A61K 37/22
[52] U.S. Cl. .................................... 424/450; 424/122
[58] Field of Search ................................ 424/450, 122

[56] References Cited

U.S. PATENT DOCUMENTS

| | | | |
|---|---|---|---|
| 4,237,117 | 12/1980 | Bruzzese et al. | 424/122 |
| 4,272,525 | 6/1981 | Wright | 514/8 |
| 4,781,871 | 11/1988 | West et al. | 424/450 |

FOREIGN PATENT DOCUMENTS

| | | |
|---|---|---|
| 2112426 | 6/1972 | France . |
| 2593394 | 7/1987 | France . |
| 87/01933 | 4/1987 | PCT Int'l Appl. . |
| 88/03831 | 4/1989 | PCT Int'l Appl. . |

OTHER PUBLICATIONS

Capuozzo et al., Biochem. Biophys. Acta, 820 (1):63-73 (1985).
Majuk, Dissertation Abstracts International, vol. 41/05-B (1980).
Mehta et al., Antimicrob. Agents Chemother., 31 (12):1901-1903 (1987).
Mehta et al., Antimicrob. Agents Chemother., 31 (12):1897-1900 (1987).
Dialog Search.
Divekar, et al., Antibiot. (Tokyo), 19 (1):63-64 (1966).
Maniar et al., Antimicrob. Agents Chemother., 5:349-352 (1965).
Maniar et al., Can. J. Microbiol., 12 (2):377-384 (1965).
Padhye, A. A., Mykosen, 12 (3):203-205 (1969).
Padhye, A. A., Sabouraudia, 7 (3):182-185 (1969).
Panse et al., Hindustan Antibiot. Bull. 8 (1):10-14 (1965).
Panse, M. V., Indian J. Exp. Biol., 5 (2):112-114 (1966).
Panse et al., Hindustan Antibiot. Bull. 16 (1):25-28 (1973).
Pansy et al., Antimicrob. Agents Chemother., 6:399-404 (1966).
Parekh et al., Life Sci., 19 (11):1737-1791 (1976).
Shadomy et al., Antimicrob. Agents Chemother., 8:452-460 (1968).
Shadomy et al., J. Bacteriol., 97 (2):481-487 (1969).
Shende et al., Hindustan Antibiot. Bull., 8 (2):51-58 (1965).
Shende et al., Hindustan Antibiot. Bull., 9 (4):229-232 (1967).
Thirumalacher et al., Sabouraudia, 4 (1):6-10 (1965).
Thirumalacher et al., Hindustan Antibiot. Bull., 9 (4):246-251 (1967).
Thirumalacher et al., Hindustan Antibot. Bull. 14 (3):123-126 (1972).
Utz et al., Antimicrob. Agents Chemother., 7:113-117 (1967).
Utz et al., Am. Rev. Respir. Dis., 95 (3):506-509 (1967).
Williams et al., Antimicrob. Agents Chemother., 5:700-705 (1965).
Williams et al., Proc. Soc. Exp. Biol. Med., 120 (2):481-484 (1965).

*Primary Examiner*—Thurman K. Page
*Assistant Examiner*—P. L. Prater
*Attorney, Agent, or Firm*—Arnold, White & Durkee

[57] ABSTRACT

The present invention involves a liposomal agent for treating disseminated fungal infection in an animal. This liposomal agent comprises a variety of polymer antifungal compounds, particularly hamycin. These antifungal compounds are encapsulated within a liposome decreasing toxicity. This liposome is preferably a stable multilamellar vesicle. The method of administration is preferably parenteral, but may be oral or topical.

19 Claims, 15 Drawing Sheets

LIPSOME-INCORPORATION OF POLYENES

The Government may own certain rights to the invention as the development of part of the present invention was supported by contract number NIAID 72639 from the National Institutes of Health, Department of Health and Human Services.

BACKGROUND OF THE INVENTION

The present invention relates to the treatment of systemic fungal infections by administration of liposomeincorporated polyenes.

Clinical observations and animal experimental studies have added to the understanding of host-fungal interactions. It is becoming recognized that host defense against fungal disease is multifactorial and may vary, depending on the etiologic agent. The mechanisms of resistance are not well defined in most instances, but various innate barriers and cell-mediated immune responses seem to be of primary importance. At this time, the role of antibody in resistance is uncertain. Clearly, debilitation of innate defenses and of cell-mediated immune responses can increase an individual's susceptibility to severe fungal disease from opportunistic agents such as *Cryptococcus neoformans* and species of Candida and Aspergillus, as well as from fungal pathogens such as *Histoplasma capsulatum* and *Coccidioides immitis*. The difficulty in gaining a complete understanding of the critical host defenses has been further complicated by many studies that show fungi may affect various host immune functions adversely. Although it is too early to evaluate the clinical importance of many of these experimental findings, investigators have demonstrated that fungi impair neutrophil function, induce IgE responses, and cause suppression of cell-mediated immune responses.

Host changes likely to be associated with increased susceptibility may be accidentally induced, as in traumatic injuries (such as burns or puncture wounds); self-induced, as in chronic alcoholism; naturally occurring, as in diabetes mellitus, various congenital immune deficiencies, collagen diseases, lymphoreticular neoplastic disease, and other types of tumors; or iatrogenically induced by instrumentation (such as catheterization), surgical procedures (such as open heart surgery), or by use of cytotoxic drugs (as in an attempt to prevent graft rejection and to treat neoplastic disease), corticosteroid therapy, and long-term use of broad-spectrum antibodies.

Chemical factors that aid resistance to fungal diseases are poorly defined. Knowledge of these substances is based primarily on circumstantial evidence at the clinical level and in vitro observations at the experimental level. Hormonally associated increases in lipid and fatty acid content on the skin occurring at puberty have been correlated with increased resistance to tinea capitis caused by the dermatophyte *Microsporum audouinii*, although pubescent changes are not the sole factors in resistance. Substances in serum, cerebrospinal fluid, and saliva may limit growth of *Cryptococcus neoformans*, and basic peptides in body fluids have been shown to inhibit *Candida albicans*.

Results of clinical and experimental studies indicate that *C. albicans*, *C. neoformans*, *Aspergillus fumigatus*, and *C. immitis* activate the alternative pathway of the complement cascade. Because of the polysaccharide nature of fungal cell walls, it is expected that all medically important fungi activate complement. Such activation may be important in defense against some mycoses; a positive correlation has been demonstrated between animals deficient in late-acting complement components (C3-C9) and increased susceptibility to fungi such as *C. neoformans* and *C. albicans*. Assuming that phagocytic cells are important in resistance to fungi, complement activation may play a role by provoking an acute inflammatory response on generation of complement fragments C3a and C5a, and by coating the fungal elements with opsonic fragments C3b and C3d for ingestion by phagocytic cells.

The systemic mycoses of humans and other animals are caused by some fungi that are pathogenic and cause disease in the healthy host, and by other fungi (opportunistic pathogens) that are usually innocuous but cause disease in patients whose immune defenses are impaired. Some of these fungi may be saprophytes in nature (soil, bird droppings), whereas others are a part of the normal human flora (commensals). In no case are humans the solitary or necessary host.

An example of a soil saprophyte is *Histoplasma capsulatum*, which commonly causes infection in endemic areas; 80%–90% of adults react positively to histoplasmin in delayed cutaneous hypersensitivity tests. An example of an opportunistic pathogen is *Candida albicans*, normally present in the oral cavity, gastrointestinal tract, and probably the skin. In the patient with acute leukemia, however, *C. albicans* is commonly present in bloo a fulminant, usually fatal, septicemia. Other opportunistic infections are seen in patients with diabetic acidosis (mucormycosis) and Hodgkin's disease (for example, cryptococcosis and histoplasmosis). The pathogenesis of these mechanisms is obscure, but cell-mediated immunity seems to be essential for a good prognosis.

Neither active vaccines nor passive immune serum immunization has been sufficiently successful to result in commercially available preparations.

Treatment of active disease may be symptomatic (for example, pain relief), sometimes surgical (resection of irremedially damaged tissue and correction of hydrocephalus), and, most successfully, chemotherapeutic (Table 1). Among the agents commonly used are hydroxystilbamidine isethionate, amphotericin B, 5-fluorocytosine (Flucytosine), miconazole, and ketoconazole. Response to these drugs varies according to the fungus, type of disease, and course of illness. For example, response is good in most *B. dermatitidis* infections, but is poor in most diseases caused by *A. fumigatus*. Response is better for skin lesions caused by *B. dermatitidis* than for meningitis due to *C. immitis*; response is better in chronic cryptococcosis than in fulminant candidiasis. Table 1 shows a listing of some systemic mycoses and generally accepted chemotherapeutic agents.

TABLE 1

CHEMOTHERAPEUTIC AGENTS FOR SYSTEMIC MYCOSES

| Disease | First Choice | Second Choice |
| --- | --- | --- |
| Aspergillosis | Amphotericin B | Ketoconazole |
| Blastomycosis | Amphotericin B | Hydroxystilbamidine isethionate |
| Candidiasis | Amphotericin B | Flucytosine or ketoconazole |
| Coccidioidomycosis | Amphotericin B | Ketoconazole |
| Cryptococcosis | Amphotericin B Flucytosine | Either drug alone* |

TABLE 1-continued

| CHEMOTHERAPEUTIC AGENTS FOR SYSTEMIC MYCOSES | | |
|---|---|---|
| Disease | First Choice | Second Choice |
| Histoplasmosis | Amphotericin B | Ketoconazole* |
| Mucormycosis | Amphotericin B | Miconazole* |
| Paracoccidioidomycosis | Amphotericin B | Sulfonamides, Ketoconazole* |

*Depending on minimal inhibitory concentration necessary for the fungus.

Infection is the cause of death in 51% of patients with lymphoma and 75% of patients with leukemia. Although bacteria are the causative organisms of many such infections, fungi account for 13% of the fatal infections in patients with lymphoma and for more than 20% of patients with leukemia. The fungus *Candida albicans* causes more than 80% of these infections, and Aspergillus spp. is also a frequent cause of such infections. In addition, fungal infection is a major cause of morbidity and mortality in patients with congenital and acquired deficiencies of the immune system. Much concerted effort has been expended in search of agents useful in treating fungal infections of humans. As a result, many compounds have been isolated and shown to have antifungal activity, but problems associated with solubility, stability, absorption, and toxicity have limited the therapeutic value of most of them in human infections. The most useful antifungal antibiotics fall into one of two categories: those that affect fungal cell membranes and those that are taken up by the cell and interrupt vital cellular processes such as RNA, DNA, or protein synthesis. Table 2 lists some useful antifungal agents and their mechanisms of action.

TABLE 2

| SOME USEFUL ANTIFUNGAL AGENTS, THEIR CHEMICAL CLASSIFICATION, AND THEIR MECHANISMS OF ACTION | | |
|---|---|---|
| Class | Compounds | Mechanism |
| Polyene | Amphotericin B Nystatin Hamycin Lucensomycin | Interacts with sterols (ergosterol) in fungal cell membrane, rendering cells selectively permeable to the outflow of vital constituents, e.g. potassium |
| Imidazole | Miconazole Clotrimazole Ketoconazole | Inhibits demethylation of lanosterol thus preventing formation of ergosterol, a vital component of fungal cell membrane; also has a direct cidal effect on fungal cells |
| Pyrimidine | 5-Fluorocytosine | Is taken up and deaminated by susceptible cell to form 5-fluorouracil, which in turn inhibits RNA synthesis; also thought to inhibit thymidylate synthetase and DNA synthesis |
| Grisan | Griseofulvin | Binds to tubulin and inhibits microtubule assembly |
| 3-Arylpyrrole | Pyrrolnitrin | Appears to inhibit terminal electron transport between succinate or NADH and coenzyme Q |
| Glutaramide | Cycloheximide | Inhibits protein synthesis at 80S ribosomal level, preventing transfer of aminoacyl tRNA to the ribosome |

TABLE 2-continued

| SOME USEFUL ANTIFUNGAL AGENTS, THEIR CHEMICAL CLASSIFICATION, AND THEIR MECHANISMS OF ACTION | | |
|---|---|---|
| Class | Compounds | Mechanism |
| | | ribosome |

The polyene macrolide antibiotics are secondary metabolites produced by various species of Streptomyces. Several common features of these compounds are useful in classifying the more than 80 different polyenes that have been isolated. All are characterized by a macrolide ring, composed of 26-38 carbon atoms and containing a series of unsaturated carbon atoms and hydroxyl groups. These features of the molecule contribute to the polyenes, amphipathic properties (those relating to molecules containing groups with different properties, for example, hydrophilic and hydrophobic). The ring structure is closed by the formation of an internal ester or lactone bond (FIG. 1). The number of conjugated double bonds vary with each polyene, and the compounds are generally classified according to the degree of unsaturation.

Toxic effects of polyene macrolides appear to be dependent on binding to cell membrane sterols. Thus, they bind to membranes of fungus cells as well as to those of other eukaryotic cells (human, plant, and protozoa), but not to bacterial cell membranes, which do not contain membrane sterols. The interaction of polyene macrolides with mammalian and fungal membrane sterols results in transmembrane channels that allow the leakage of intracellular components leading to cell deaths.

The usefulness of an antibiotic is usually measured by the differential sensitivity of the pathogen and host. The polyene macrolide compounds, for example, hamycin and lucensomycin, are relatively specific for fungi and are potentially useful in humans. The relative specificity of these two polyene macrolides is based on their greater avidity for ergosterol, the principal sterol of fungal membranes, compared to cholesterol, the principal sterol of human cell membranes. However, it is the binding to cholesterol which causes the toxicities typically associated with the polyene macrolide compounds. Because the polyene macrolides are so potentially useful, researchers are actively investigating ways to reduce the toxic effects of these compounds.

It has recently been shown that the encapsulation of certain drugs in liposomes before administration to the patient can markedly alter the pharmacokinetics, tissue distribution, metabolism and therapeutic efficacy of these compounds. Liposomes may be defined as lipid vesicles which are formed spontaneously on addition of an aqueous solution to a dry lipid film. Further, the distribution and pharmacokinetics of these drugs can be modified by altering the lipid composition, size, charge and membrane fluidity of the liposome in which they are encapsulated.

Recently, liposomes have been used as carriers of Amphotericin B for treatment of murine leishmaniasis (New, R. R. C., et al., "Antileishmanial Activity of Amphotericin and Other Antifungal Agents Entrapped in Liposomes." *J. Antimicrob. Chemother.*, Vol. 8 (1981), pp. 371-381), histoplasmosis (Taylor, R. L., et al., "Amphotericin B in Liposomes: A Novel Therapy for histoplasmosis." *Am. Rev. Respir. Dis.*, Vol. 125 (1982), pp. 610-611), cryptococosis (Graybill, J. R., et al., "Treatment of Murine Cryptococosis with Liposome-Associated Amphotericin B." *J. Infect. Dis.*, Vol. 145 (1982), pp. 748-752). and candidiasis (Tremblay, C., et al., "Comparative Efficacy of Amphotericin B (AMB) and Liposomal AMB (lip-AMB) in Systemic Candidiasis in Mice." *Abstr.* 1983 *ICAAC*, No. 755 (1983), p. 222). Liposome-encapsulated Amphotericin B has also been used for treatment of coccidioidomycosis in the Japanese macaque (Graybill, J. R., et al., "Treatment of Coccidioidomydosis (cocci) in Primates Using Liposome Associated Amphotericin B (Lipo-AMB)." *Abstr.* 1982 *ICCAC*, No. 492 (1982), p. 152).

The present inventors have recently demonstrated that liposome encapsulated amphotericin B (AmpB) may be used to treat experimental murine candidiasis (Lopez-Berestein et al., J. Infect. Dis., Vol. 120, pp 278-283 (1984) and in the treatment of fungal infections in patients with leukemia and lymphoma (Lopez-Berestein et al., J. Infect. Dis., Vol. 151, pp 704-71- (1985).

Liposome encapsulation has markedly reduced the toxicity and enhanced the therapeutic index of polyene macrolide compounds. However, liposome formulations presently available do not sufficiently reduce toxicity of several polyene macrolide compounds, for example, hamycin, lucensomycin, and mepartricin. Accordingly, these drugs are not widely available as therapeutic agents. Recently, the present inventors have discovered that by increasing the percentage of cholesterol in the liposome formulation, the toxicity typically associated with polyene macrolide compounds is greatly reduced. Thus, the present inventors have demonstrated that liposome formulations having cholesterol concentrations as high as 60% by weight increased the rate of survival in mice treated with polyene macrolide compounds threefold. In these studies, the present inventors demonstrated that liposomes containing a large percentage by weight of cholesterol, reduced the toxicity of polyene macrolide compounds so that they may now be used relatively safely.

SUMMARY OF THE INVENTION

The present invention involves a liposomal agent for treating disseminated fungal infection in an animal. This liposomal agent comprises lipids, a polyene macrolide antifungal compound, and cholesterol. The cholesterol is included in concentrations of from 10 to 75% by weight. It has been determined that as the concentration of cholesterol in the liposome increases, the toxicity of the incorporated polyene macrolide compound decreases. The polyene macrolide antifungal compound is incorporated in or encapsulated within a liposome for effective therapy of systemic fungal infection.

The liposome in which the polyene macrolide compound is incorporated is preferably a multilamellar vesicle. The liposome includes one or more lipids, preferably phospholipids, selected from the group consisting of phosphomonoglyceride, phosphatidic acid and sphingolipid. The lipids are more preferably one or more of phosphatidylcholine, phosphatidylserine, phosphatidylglycerol, sphingomyelin or phosphatidic acid. The lipids are most preferably selected from the group consisting of dimyristoyl phosphatidylcholine, dimyristoyl phosphatidylglycerol, phosphatidylcholine and phosphatidylglycerol.

The liposome of the present invention also comprises a sterol, preferably cholesterol. The sterol is included in a high concentration, from about 10 to 75% by weight. It has been demonstrated that these high concentrations of sterols drastically reduces the toxicity typically associated with polyene macrolide compounds.

An important aspect of the present invention involves a method for treating disseminated fungal infection in an animal. This method comprises administering to an animal subject to disseminated fungal infection, a fungicidally effective amount of a polyene macrolide antifungal compound encapsulated within a liposome. The liposome is composed as described above. The method of administration is preferably parenteral in most instances, but may be oral or topical if specific colonies of fungus are thereby more directly reached. Parenteral treatment is most useful when the animal is a human suffering from disseminated fungal infection. The method of treatment involves administering a fungicidally effective amount of liposome-incorporated polyene compound of between about 0.1 mg/kg body weight and about 80 mg /kg body weight.

An additional aspect of the present invention involves a method of treating various other diseases such as benign prostate hyperplasia and hypercholesterolemia and inflammation. Moreover, the present invention may be used in conjunction with other drugs to enhance their efficiency and produce synergistic effects.

Yet another important aspect of the present invention is to provide an optimal liposomal formation which significantly buffers the toxicity of mepartricin, hamycin and lucensomycin, as well as other small polyenes (i.e., filipin, lagosin and natamycin).

DETAILED DESCRIPTION OF THE PREFERRED EMBODIMENT

Figure 1:
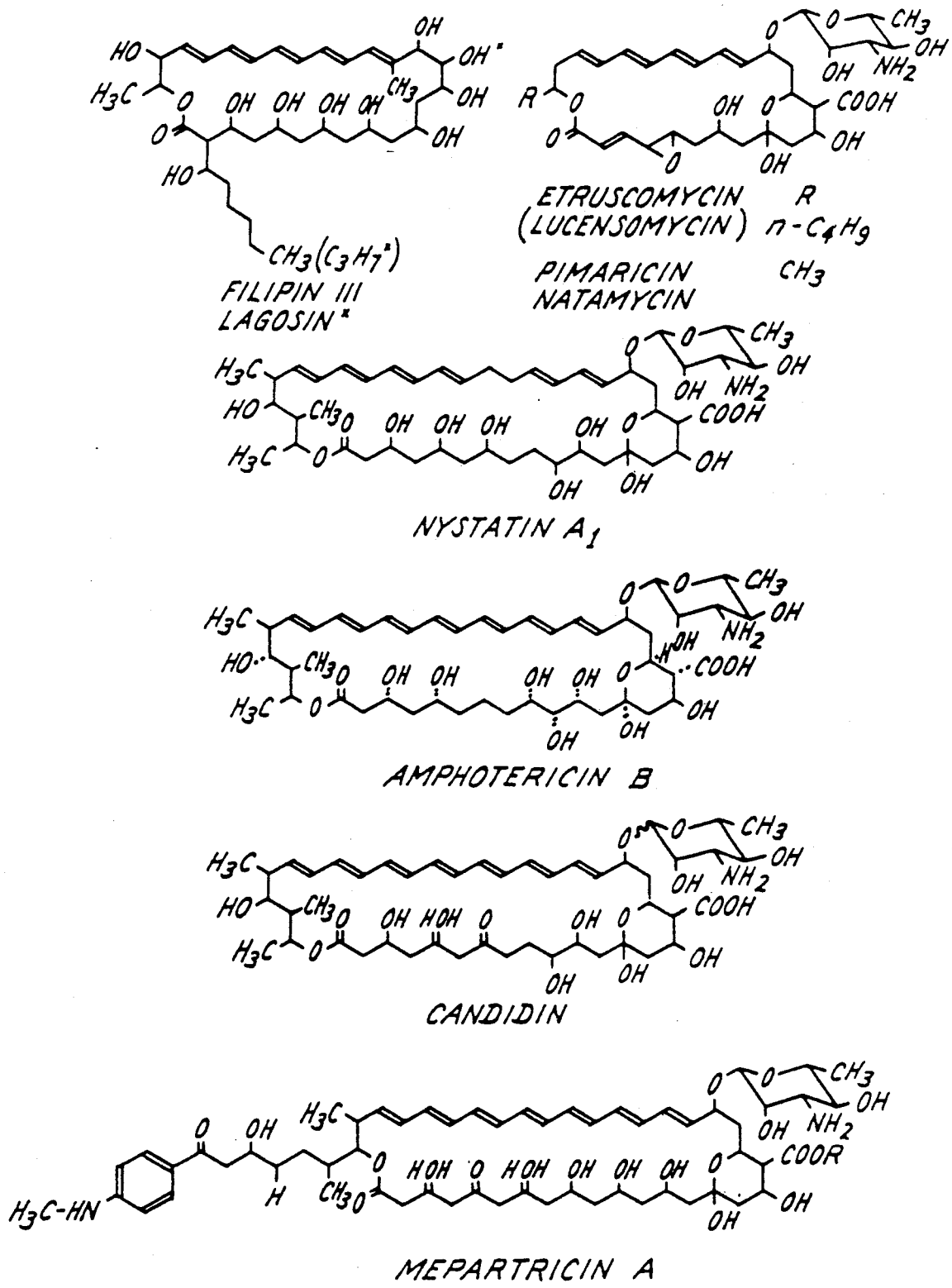
FIG. 1 shows the structures of the polyenes studied.

The use of polyene macrolide compounds encapsulated in liposomes including a high percentage of cholesterol for the treatment of disseminated fungal infections is described herein as a new effective therapeutic method particularly useful for treatment of systemic or disseminated fungal infections. It has been demonstrated that hamycin, lucensomycin and mepartricin encapsulated in a liposome including a large percentage of cholesterol have lowered systemic toxicity and an enhanced therapeutic efficiency as compared to other dosage forms.

Although hamycin encapsulated in liposomes having no or low cholesterol concentrations had antifungal activity in vitro, such it was toxic and noneffective in vivo (i.e., when administered intravenously.) A reduced in vivo toxicity was observed with liposomal-hamycin including a large percentage of cholesterol, while the antifungal properties were maintained. Similarly, the toxicity of mepartricin in vivo was found to be significantly reduced when encapsulated in liposomes.

Liposomes have been extensively used to modify the therapeutic index of polyene compounds. The present inventors have previously demonstrated that liposomes enhance the delivery of amphotericin B to infected sites (Lopez-Berestein et al., (1968) *Cancer Drug Delivery*, 1:199–205), thus promoting the drug-drug carrier interactions with systemic fungi. The observation with encapsulated polyene drugs has been that the improvement in their therapeutic index was related to the reduced toxicity of free-drug after encapsulation.

Nevertheless, presently available liposome formulations still do not sufficiently reduce polyene macrolide toxicity. An important aspect of the present invention involves liposomes comprising a high percentage of cholesterol in association with lipids and a polyene macrolide compound, as well as the preparation and uses of these liposomes. Liposomes of the present invention include cholesterol in a preferred range of between from about 10 to about 75 percent by weight, a more preferred range being between about 30 to about 60 percent by weight. The polyene macrolide compound may be part of the phospholipid lamellae, part of the encapsulated intraliposomal fluid or both.

Preferred phospholipids of these liposomes include phosphatidylglycerol, phosphatidylcholine, sphingomyelin, phosphatidic acid or phosphatidylserine, the more preferred phospholipids being phosphatidylglycerol, phosphatidylcholine, dielaidyl phosphatidylcholine, phospholatidylethanolamine, dideoyl phosphatidylcholine or a combination thereof. The most preferred phosphatidylglycerol is one consisting essentially of dimyristoyl phosphatidylglycerol and the most preferred phosphatidylcholine is one consisting essentially of dimyristoyl phosphatidylcholine. When the liposomes of the present invention comprise dimyristoyl phosphatidylglycerol and dimyristoyl phosphatidylcholine they are preferably in a ratio between about 1:10 and 10:1, more preferably in a ratio of about 3:7. The lipids of the present invention preferably comprise from about 25 to about 90 percent by weight of the liposome. Most preferably, however, the lipids comprise from about 25 percent to about 45 percent by weight of the liposome.

The liposomes of the present invention may be multilamellar, unilamellar or have an undefined lamellar construction. A pharmaceutical composition comprising the liposomes of the present invention and a pharmaceutically acceptable carrier or diluent of the types well known to those skilled in the art may be used for the therapy of disease conditions involving local or systemic fungal infections.

Such liposomes may be administered parenterally, topically or orally, parenterally being preferred for systemic or disseminated fungal infections. Parenteral dosages of polyene macrolide compounds are generally in fungicidally effective amounts between about 0.1 mg/kg body weight to about 80 mg/kg body weight and are contemplated as adequate in most conditions. The particular dosages, if an infected human is being treated, will vary in each case according to the condition of the patient, the type and extent of fungal infection, the polyene macrolide compound used, and directions of an attending physician.

Preferably, the polyene macrolide compound of the present invention is at least one selected from the group consisting of hamycin, lucensomycin, nystatin, amphotericin B, mepartricin, candidin, filipin, lagosin, and natamycin. However, it is most preferred that the polyene macrolide compound is one or more selected from the group consisting of hamycin, lucensomycin and mepartricin.

A focal point of the present invention involves a method of treating a host animal afflicted with a fungal infection. This method comprises administering to the host an amount of a liposome of the present invention comprising a high percentage of cholesterol, a phospholipid, and an effective fungus-inhibiting amount of a polyene macrolide compound. The mode of administration is preferably parenteral, i.e. by intravenous, intraarterial, intramuscular, intralymphatic, intraperitoneal, subcutaneous, intrapleural or intrathecal injection or infusion, topical application or oral dosage. Such administration is preferably repeated on a timed schedule, for example twice daily for a period of two weeks. The treatment may be maintained until the fungus has been eliminated and may be used in conjunction with other forms of anti-fungal therapy or support therapy. Such parenteral administration preferably involves suspensions of polyene macrolide compounds in pharmaceutically acceptable solutions such as sterile isotonic aqueous solutions. These suspensions may be obtained fully prepared or may be prepared from preformed components. As known to those skilled in the art, polyene macrolide compounds may be prepared and mixed with pharmaceutically acceptable solutions to form suspensions for parenteral administration.

Topical administration of the polyene compound may involve pharmaceutical compositions such as suspensions, creams or ointments which may be obtained fully prepared or prepared spontaneously. Such topical administration may be near to sites of localized fungal infection, such as the epithelium or mucosa.

Oral administrations of polyene macrolide compounds preferably involve encapsulation to protect them from gastric and intestinal digestive activities before release from encapsulation.

The methods of preparation of the liposome of the present invention and chemotherapeutic treatment are herein described in the following Examples, and are readily adapted to the production and use of analogously described liposomes by simple substitutions of appropriate lipids or methods.

Liposomes containing polyene macrolide compounds described herein may be prepared from various amphipathic substances including natural or synthetic phospholipids. The phospholipids usable to produce liposomes are numerous and are not exhaustively listed herein because they are generally well known in the art. These phospholipids include but are not limited to: lecithin, phosphatidylethanolamine, lysolecithin, lysophosphatidyl ethanolamine, phosphatidylserine, phosphatidylinositol, sphingomyelin, cardiolipin, phosphatidic acid and the cerebrosides. Most preferable phospholipids for the practice of aspects of the present invention include dimyristoyl phosphatidylglycerol (DMPG) and dimyristoyl phosphatidylcholine (DMPC). The liposome may further comprise a sterol such as cholesterol. The sterol is to be included in proportions ranging from about 10% to about 75% by weight with the phospholipids and polyene compound to produce liposomes of the present invention. A preferable but not limiting combination of DMPG and DMPC has been found to be a ratio of 3 to 7, although ratios between 1:10 and 10:1 are contemplated as satisfactory. Either unilamellar, multilamellar or other polyene compound-containing mixed micellar preparations may be used in the practice of the present invention.

The liposome-encapsulated polyene compounds of the present invention also may prove useful in the prophylaxis and/or treatment of disease caused by human T lymphotropic retrovirus, designated HTLV-III/LAV. As Gallo recently pointed out, HTLV-III/LAV may be carried in vivo by monocytes and macrophages (in *Scientific American*, (1987) January, pp 47–56). These cell types may thus serve as potentially infectious and deadly HTLV-III/LAV reservoirs.

In a recently published study, Schaffner et al. (1986), *Biochem. Pharmacol.*, 35:4110–4113) showed data indicating that the replication of HTLV-III/LAV in the monocyte-related cell line $H^9$ was inhibited by several antifungal polyene macrolides. These polyene macrolides included amphotericin B and amphotericin B methyl ester ascorbate.

The phagocytes of the blood—monocytes, macrophages and polymorphonuclear leukocytes—characteristically bind and ingest foreign substances, even prior to an immune response. These phagocytes also are among the first cells to take up circulating liposomes. It appears likely that parenteral administration to an animal of liposomes comprising a polyene macrolide should be useful to inhibit intracellular HTLV-III/LAV proliferation. The liposomeinduced increased bioactivity of nystatin may prove important in the control of disease caused by HTLV-III/LAV infection.

These following examples are presented to describe preferred embodiments and utilities of the present invention but are not meant to limit the present invention unless otherwise stated in the claims appended hereto. For example, although dimyristoyl phosphatidylglycerol and dimyristoyl phosphatidylcholine were used to form liposomes, these particular lipid forms are by no means the only available usable lipids known to those skilled in the art. Nor do the particular formation methods for or types of liposomes used in these examples represent the only usable methods or liposome types.

EXAMPLE 1

Drug, Lipids and Reagents

Hamycin (bulk powder) was obtained from National Chemical Laboratory (India). Chromatographically pure dimyristoyl phosphatidylcholine (DMPC) and dimyristoyl phosphatidylglycerol (DMPG) were purchased from Avanti Polar Lipids (Birmingham, Ala.). Methanol for high-performance liquid chromatography (HPLC), dimethyl sulfoxide (DMSO), and N,N-dimethylformamide (DMFA) were purchased from Fisher Scientific (Fair Lawn, N.J.). Human AB serum was from MA Bioproducts (Walkersville, Md.). Human RBCs were obtained from normal volunteers.

EXAMPLE 2

Liposome Preparation and Standardization

Multilamellar vesicles (MLV) were prepared as described previously (Lopez-Berestein et al., *J. Infect. Dis.*, 278–283 (1984)). Cholesterol, phospholipids, and the phospholipids DMPC:DMPG (7:3), were mixed with increasing amounts of the hamycin and the organic solvents evaporated under vacuum using a rotary evaporator. The dried cholesterol-lipid-drug film was suspended in phosphate-buffered saline (PBS) and handshaken, allowing the film to form liposomes. The suspensions were then recovered from the flasks and centrifuged at 20,000 rpm for 1 hr. The pellets were resuspended in PBS and the percentage of hamycin incorporated in liposomes was determined by absorbance at 380 nm. Similarly, hamycinliposomes composed of phospholipids and without sterols were also prepared. The following Table 3 shows the characteristic properties of these liposomes.

The stability of hamycin-liposomes was assessed by incubating equal amounts of hamycin-liposomes with PBS and human AB serum at 37° C. At indicated time intervals, samples were taken out, centrifuged at 10,000 × g for 15 min and hamycin concentration in the pellet was measured. Hamycin-liposomes were stable up to 2-3 months and retained 60 to 80 percent of the drug after three months or storage at 4° C.

TABLE 3

| LIPOSOME PREPARATION | | | |
|---|---|---|---|
| Name of the drug | Hamycin | | |
| Source | National Chemical Laboratory Pune, INDIA | | |
| Chemical structure | Polyene | | |
| | | 1 mg/ml | Maximum solubility |
| Solubility | 1. Water/saline | Nil | — |
| | 2. Ethanol | Soluble | 40 ug/ml |
| | 3. Methanol | Partial | 100 ug/ml |
| | 4. DMFA | Yes | 10 mg/ml |
| | 5. DMSO | Yes | 20 mg/ml |
| | 6. Chloroform | Nil | |
| Quantitation | UV absorption at 380 nm | | |
| Encapsulation | 1. DMPC:DMPG (7:3) | | 70% |
| efficiency | 2. DMPC:DMPG:cholesterol (6:3:1) | | 68% |
| | Time | | % retention |

TABLE 3-continued

| LIPOSOME PREPARATION | | | |
|---|---|---|---|
| Stability | (a) Saline (b) Serum | 3 months | 60–80% |
| Drug/Lipid ratio | | 1:10 | |

EXAMPLE 3

Encapsulation Efficiency of Hamycin in Liposomes

The encapsulation efficiencies were calculated for different batches of liposomes prepared with a fixed amount of liposome and increasing doses of hamycin. The maximum incorporation was 68% obtained at a drug/phospholipid ratio of 1:10.

EXAMPLE 4

In vitro fungal inhibition

The antifungal activity of free- verses liposomalhamycin against *Candida albicans* (strain 336) was determined in vitro. All strains of yeast were grown overnight at 37° C. on Sabouraud dextrose agar (SDA) plates. All molds were grown at 30° C. on SDA for 3 to 10 days prior to collection of spores. The inoculum was then processed for susceptibility testing as described earlier (Hopfer et al. (1984), *Antimicrob. Agents Chemotherap.*, 25:387–389). A twofold serial dilutron method (Shadomy et al., In E. H. Lennette, et al., (eds.) Manual of Clinical Microbiology, 3rd ed. American Society for Microbiology, Washington, D.C. , pp. 647–653 (1980)) adapted to microtiter plates was used to determine the minimal inhibitory concentration (MIC) of the drugs. The MIC of free-hamycin was compared with that of liposomal-hamycin.

The MIC of free-hamycin was 0.25 microgram/ml (Table 3) and the MIC for liposomal-hamycin was 0.36 microgram/ml. The antifungal activity was thus maintained in liposomal-hamycin with or without cholesterol.

EXAMPLE 5

Toxicity of Free-Hamycin and LiposomalHamycin to human RBC's in vitro

Lysis of human red blood cells (RBCs) was quantitated by measuring the release of hemoglobin in the supernatants at 540 nm, as described previously (Mehta et al., (1984) *Biochem. Biophys, Acta.*, 770:230–234). Various doses of liposomalhamycin were incubated with fresh washed human RBCs at 37° C. for 45 min. Free-hamycin, dissolved in dimethyl formamide (DMFA), was added to the assay at a 3% final solvent concentration. Release of hemoglobin by hypotonic lysis of the same number of human RBCs by water was taken as 100% positive control, while cells treated with PBS were taken as negative controls.

Figure 2:
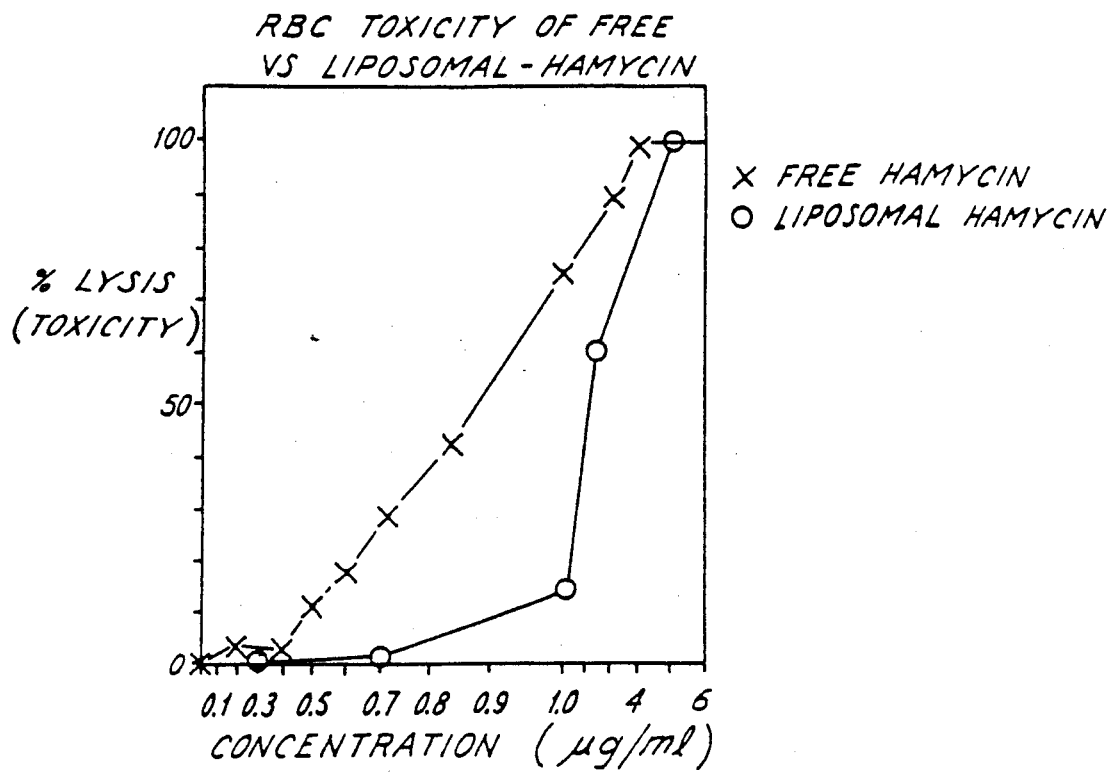
FIG. 2 shows the in vitro toxicity of free-hamycin versus liposomal-hamycin to human RBCs. The human RBCs re incubated at 37° C. for 45 minutes with (X) and ( ) liposomal-hamycin.
Figure 3:
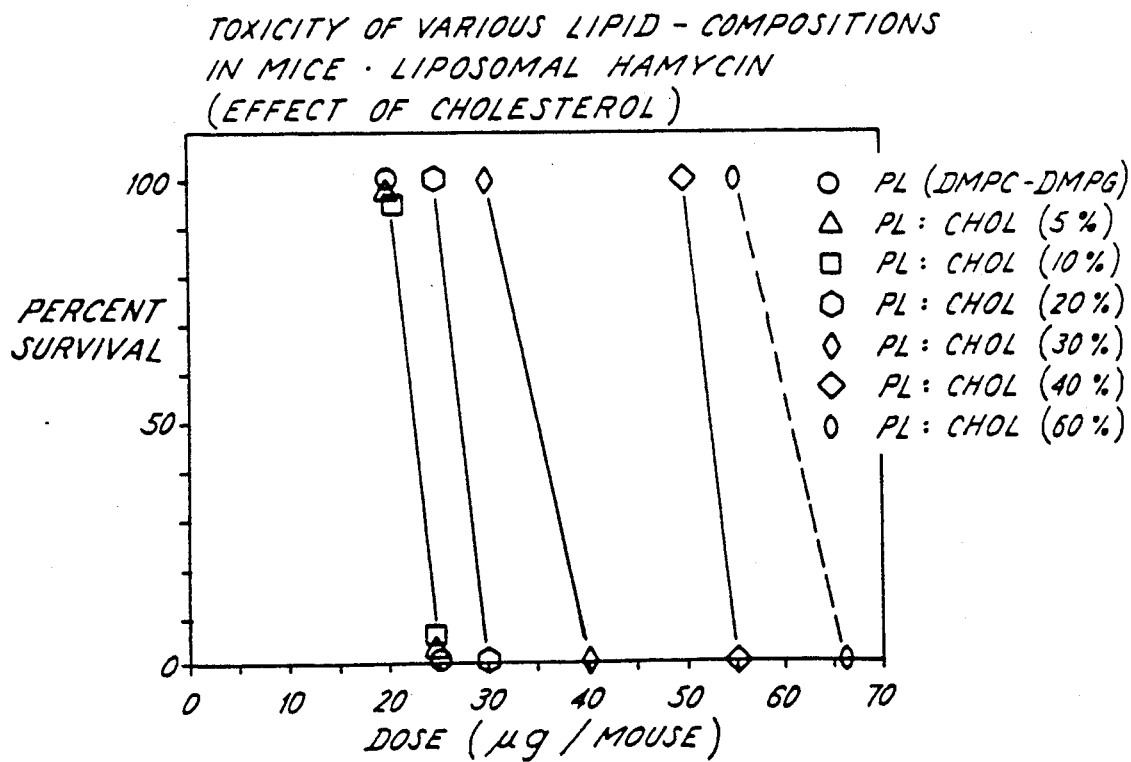
FIG. 3 shows the toxicity of various lipidcompositions of liposomal hamycin having varying concentrations of cholesterol. Mice were dosed with various amounts of hamycin incorporated into liposomes having increasing amounts of cholesterol. Specifically, the liposomal compositions were ( )PL (DMPC-DMPG), ( )PL:CHOL (cholesterol) (5%), ( ) PL:CHOL (10%), ( ) PL:CHOL (20%), (△) PL:CHOL (30%), (□) PL:CHOL (40%), and ( ) PL:CHOL (60%).

A linear increase in lysis of human RBCs was observed with free-hamycin ranging from 0.4 to 4.0 ug/ml, with 100% lysis produced at 4.0 ug/ml (FIG. 2). In contrast, liposomal-haxycin did not cause any lysis with doses up to 0.7 mg/ml. Both hamycin preparations were equally toxic at doses higher than 5 mg/ml.

EXAMPLE 6

Toxicity of Free-Hamycin and Liposomal-Hamycin Prepared without Cholesterol to human RBC's in vitro Lysis of human red blood cells (RBCs) was quantitated by measuring the release of hemoglobin in the supernatants at 540 nm, as described previously (Mehta et al., Biochem. Biophys, Acta., Vol. 770, pp. 230–234 (1984)). Various doses of liposomal-lucensomycin prepared without cholesterol were incubated with fresh washed human RBCs at 37° C. for 45 min. Free-hamycin, dissolved in dimethyl formamide (DMFA), was added to the assay at a 3% final solvent concentration. Release of hemoglobin by hypotonic lysis of the same number of human RBCs by water was taken as 100% positive control, while cells treated with PBS were taken as negative controls.

Figure 5:
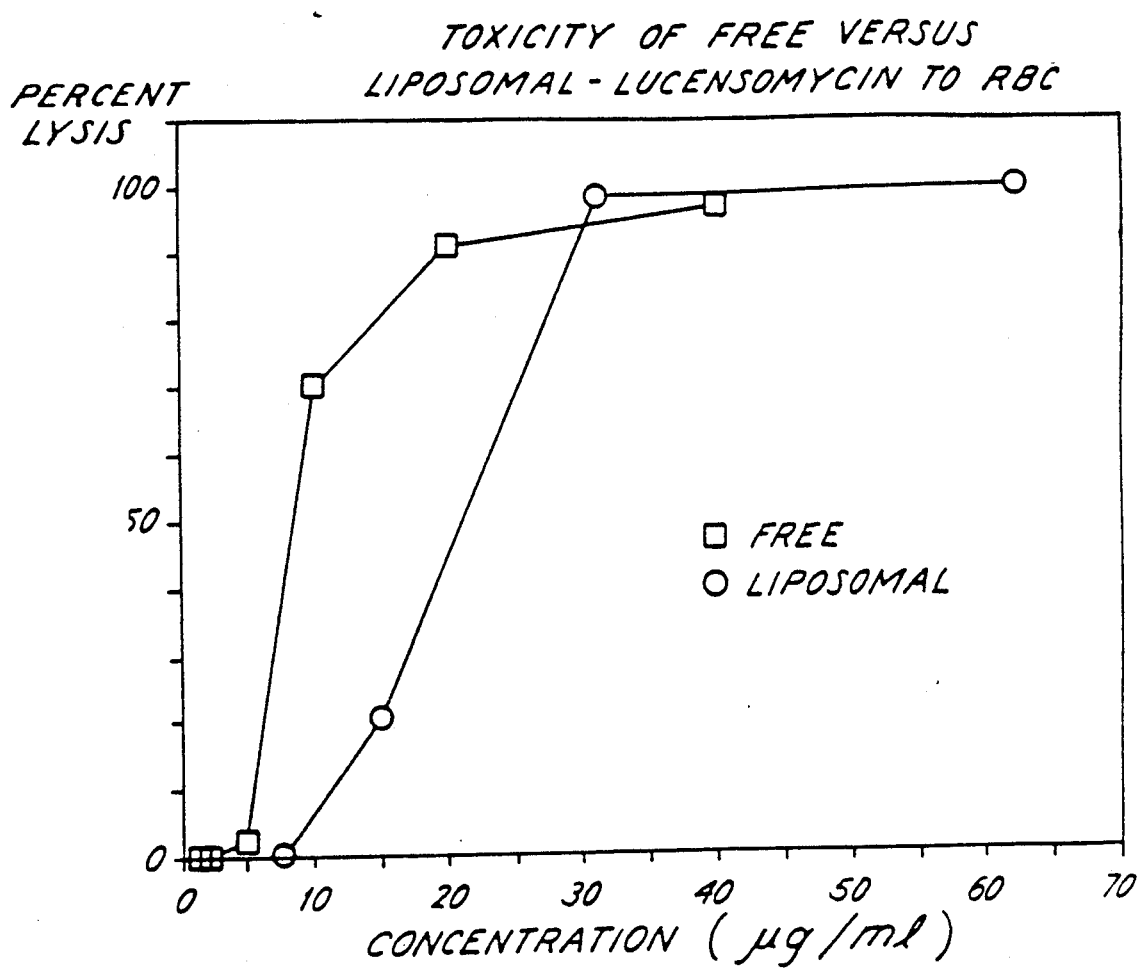
FIG. 5 shows the in vitro toxicity of free-lucensomycin versus liposomal-lucensomycin to human RBCs. The human RBCs were incubated at 37° C. for 45 minutes with ( ) free-lucensomycin and ( ) liposomal-lucensomycin.
Figure 6:
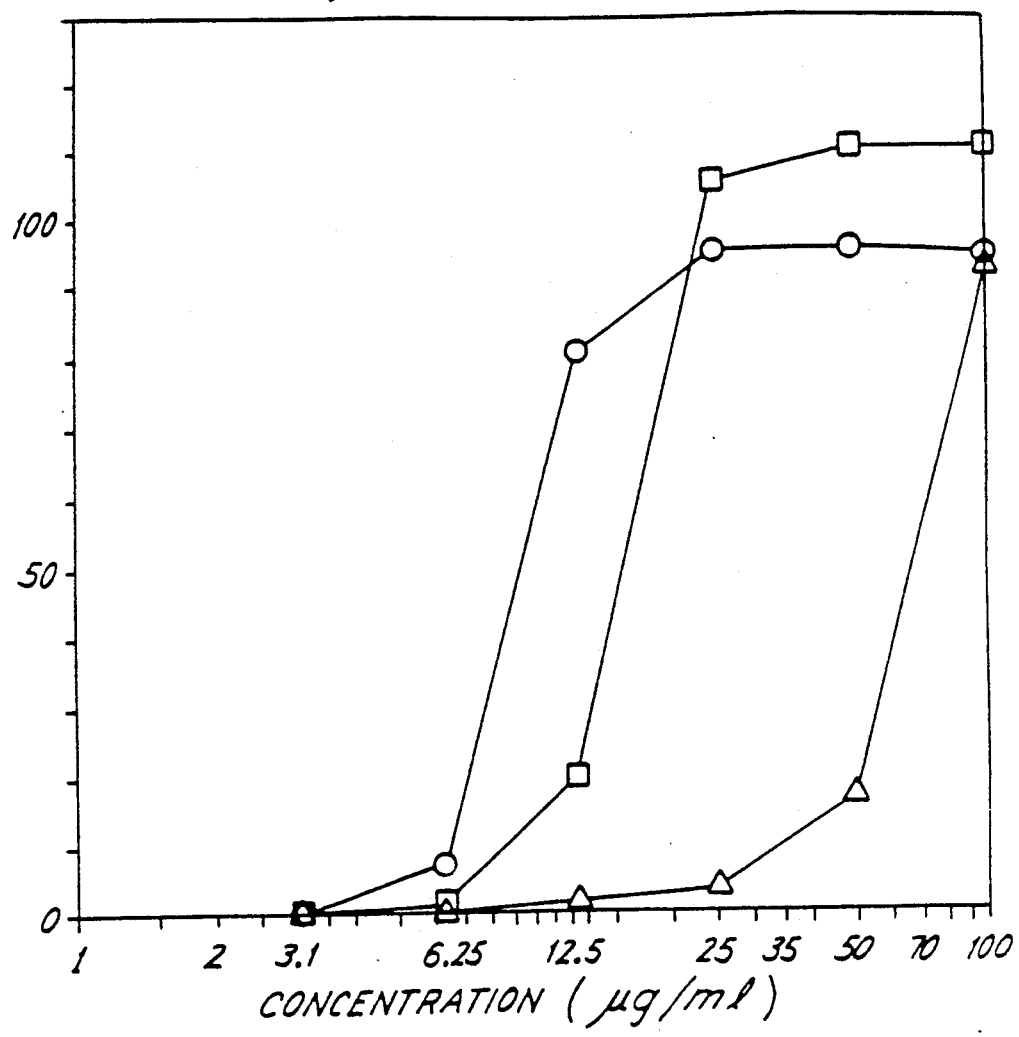
FIG. 6 shows the in vitro toxicity of liposomallucensomycin having varying concentrations of cholesterol to human RBCs. The human RBCs were incubated at 37° C. for 45 minutes with ( ) cholesterol concentration 20%, ( ) cholesterol concentration 40%, ( ) cholesterol concentration 60%.
Figure 7A:
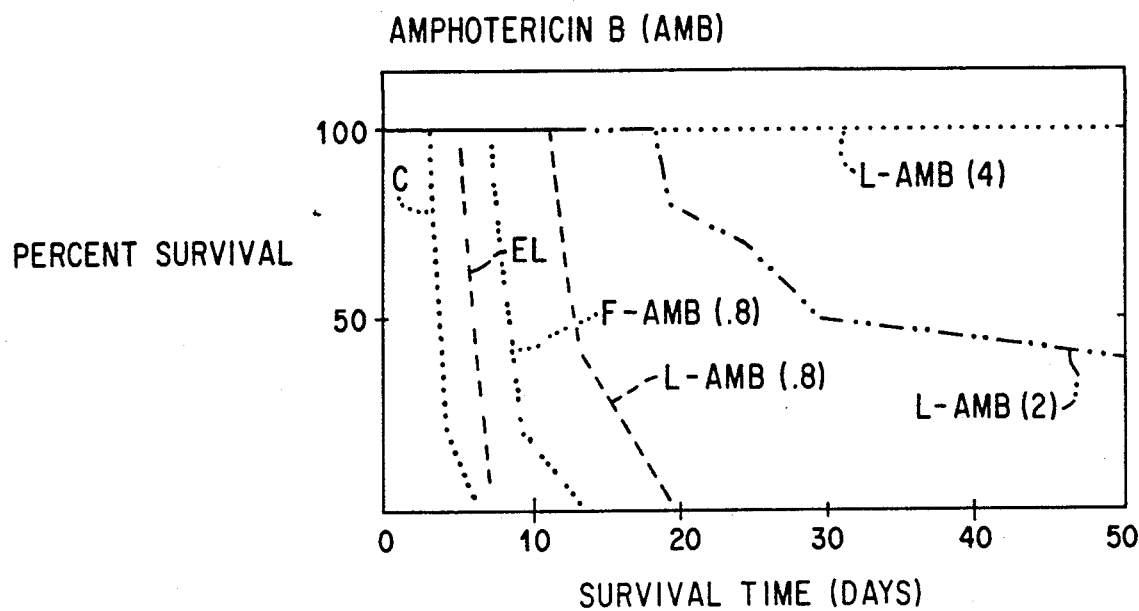
FIG. 7 shows the in vivo toxicity of free verses liposome-encapsulated large polyenes in mice.
Figure 7B:
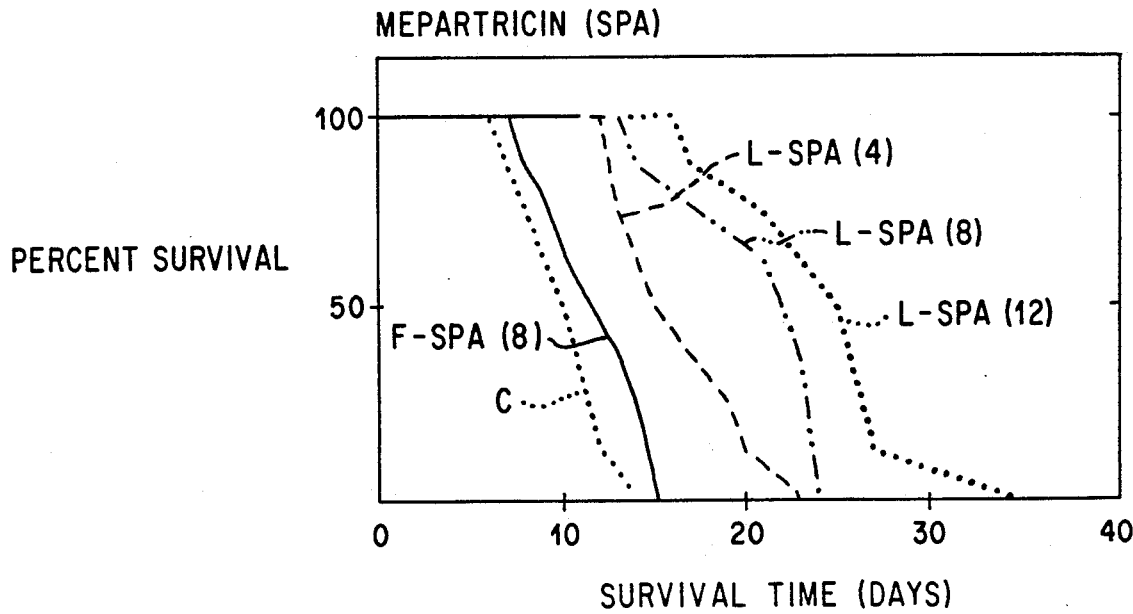
Figure 7C:
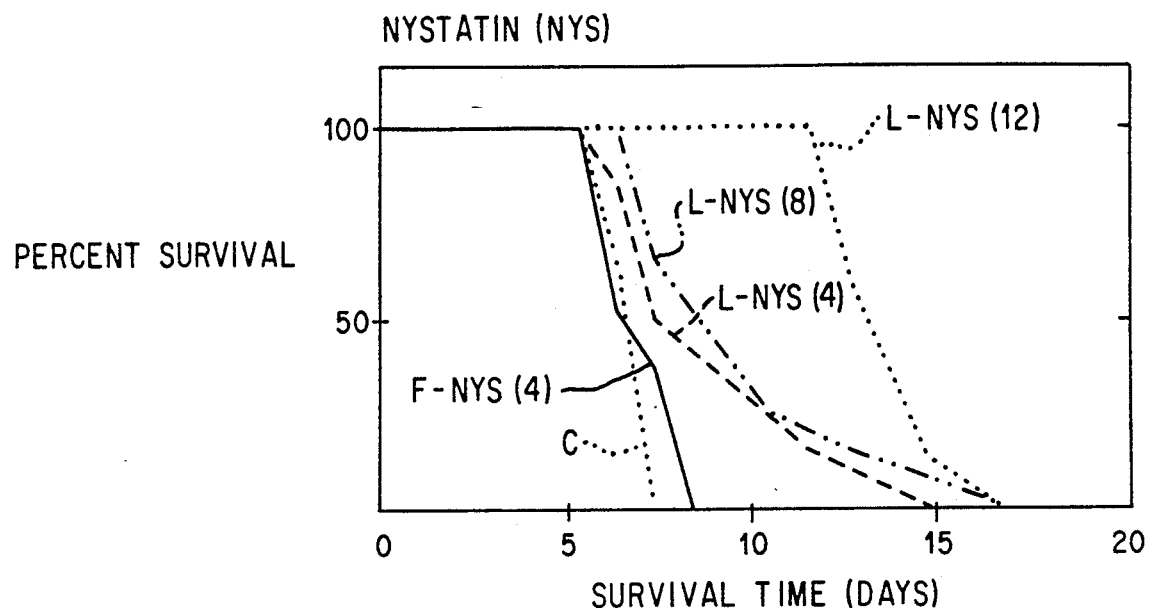
Figure 7D:
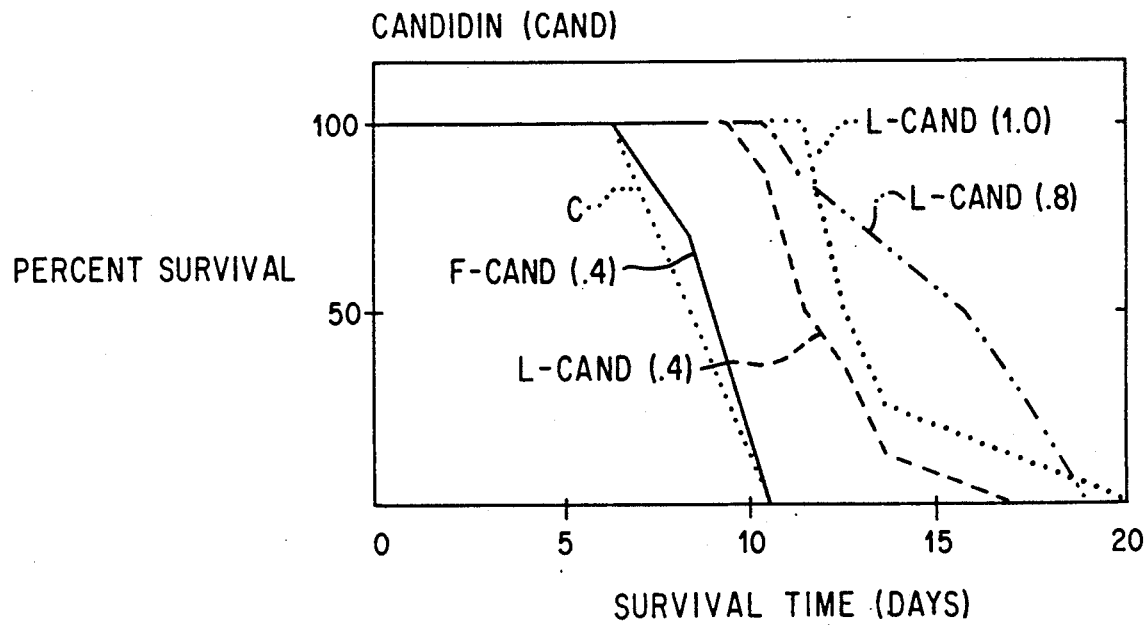
Figure 8A:
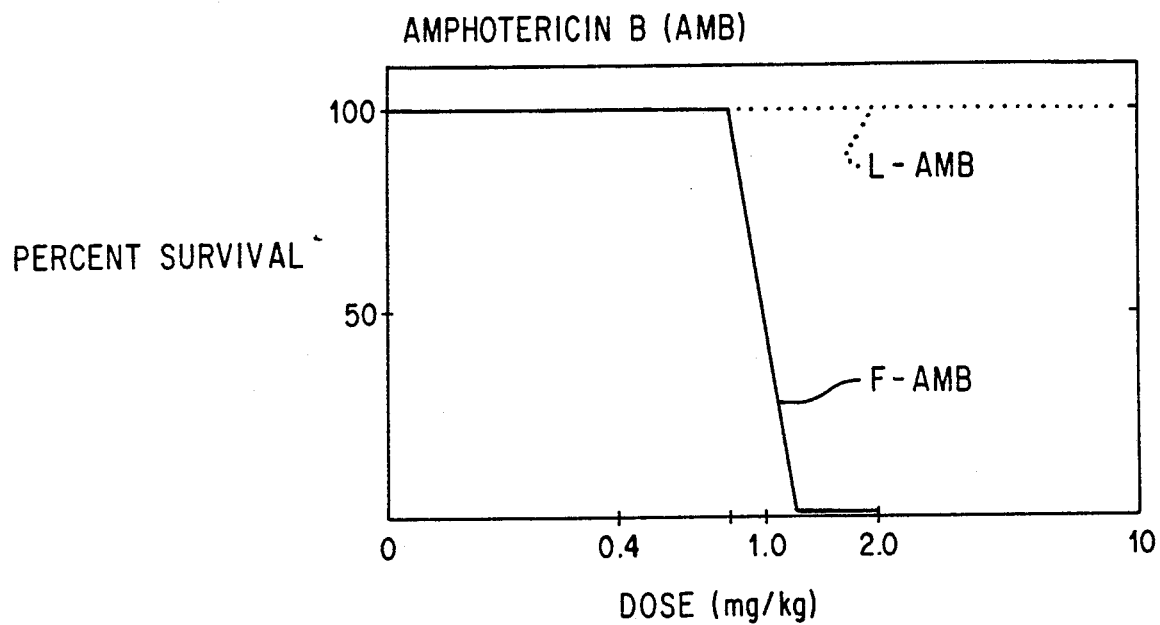
FIG. 8 shows the in vivo toxicity of liposomalmepartricin with different lipid compositions. Specifically, this figure represents the percent survival of mice administered various doses of mepartricin encapsulated in the following liposomal formulations: DEPC:PE:-CHOL, PC:CHOL, DOPC:PE:CHOL, Free-mepartricin, DMPC:DMPG.
Figure 8B:
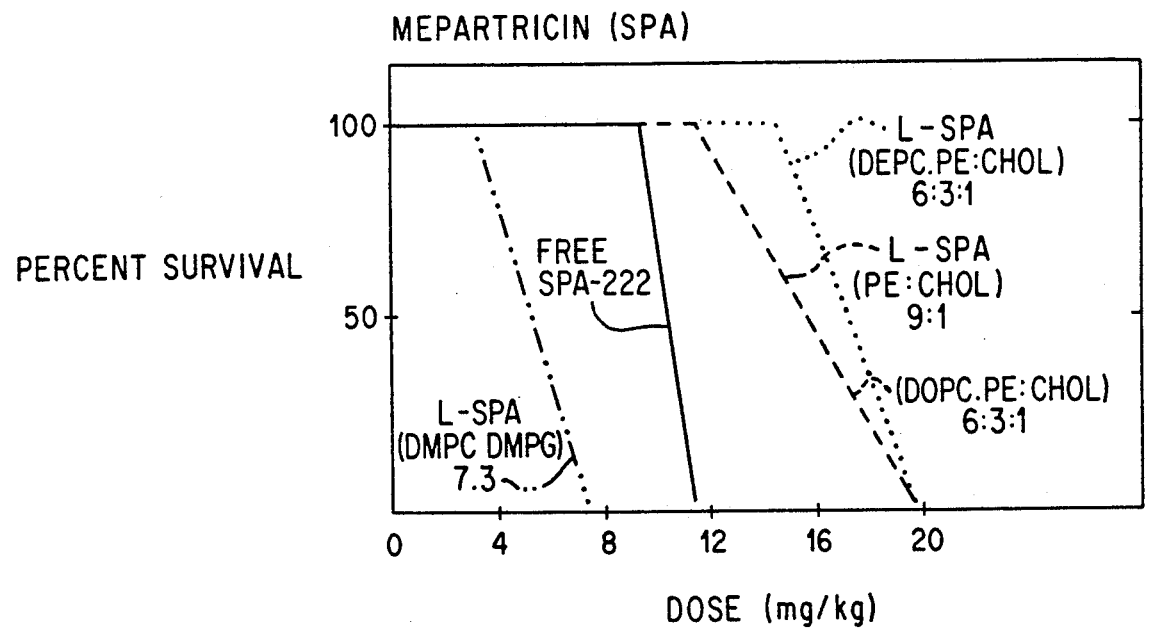
Figure 8C:
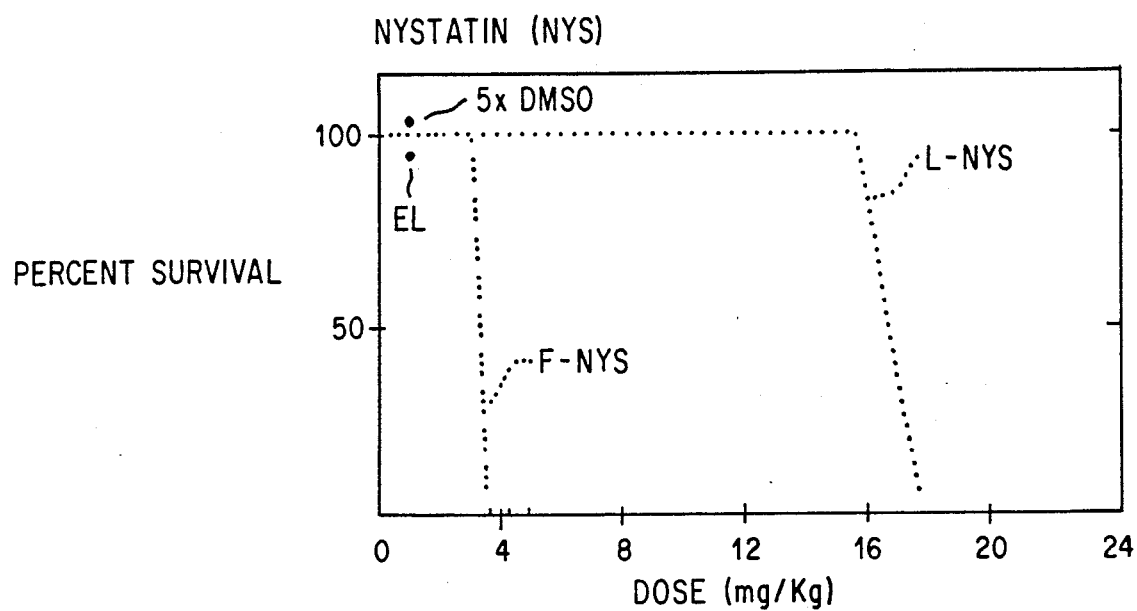
Figure 8D:
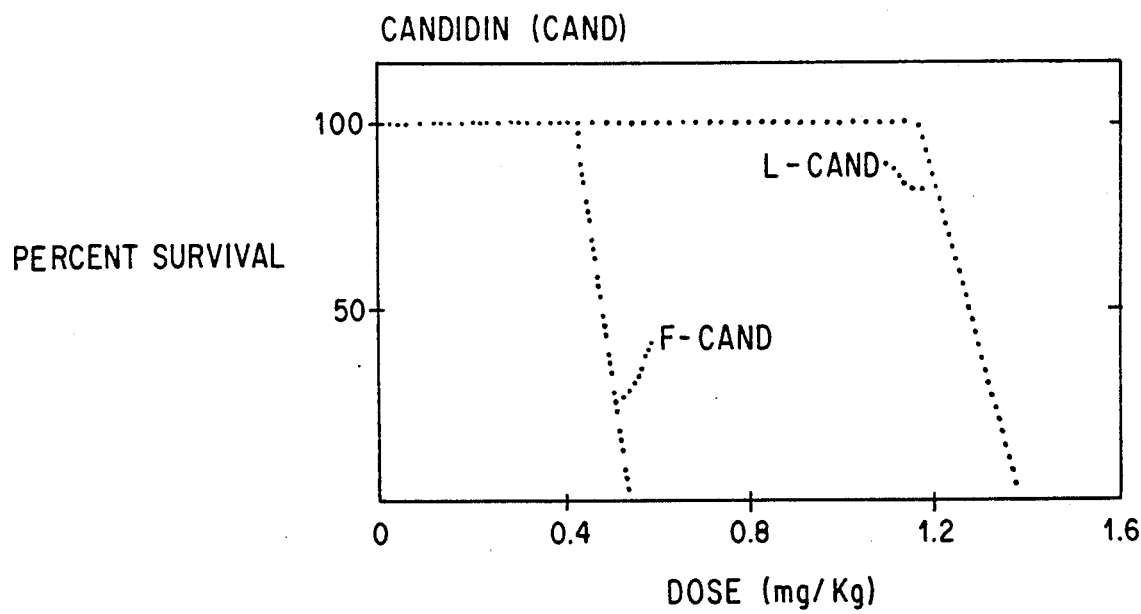
Figure 9A:
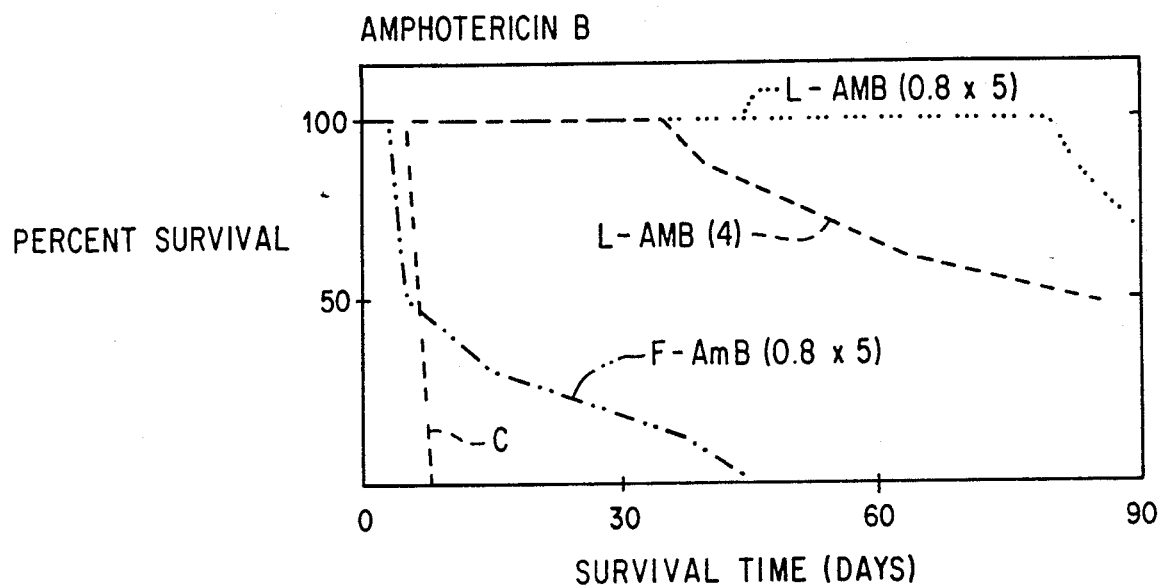
FIG. 9 shows the survival of mice treated with multiple doses of free or liposome-encapsulated large polyenes, including mepartricin, two days after infection with *Candida albicans*.
Figure 9B:
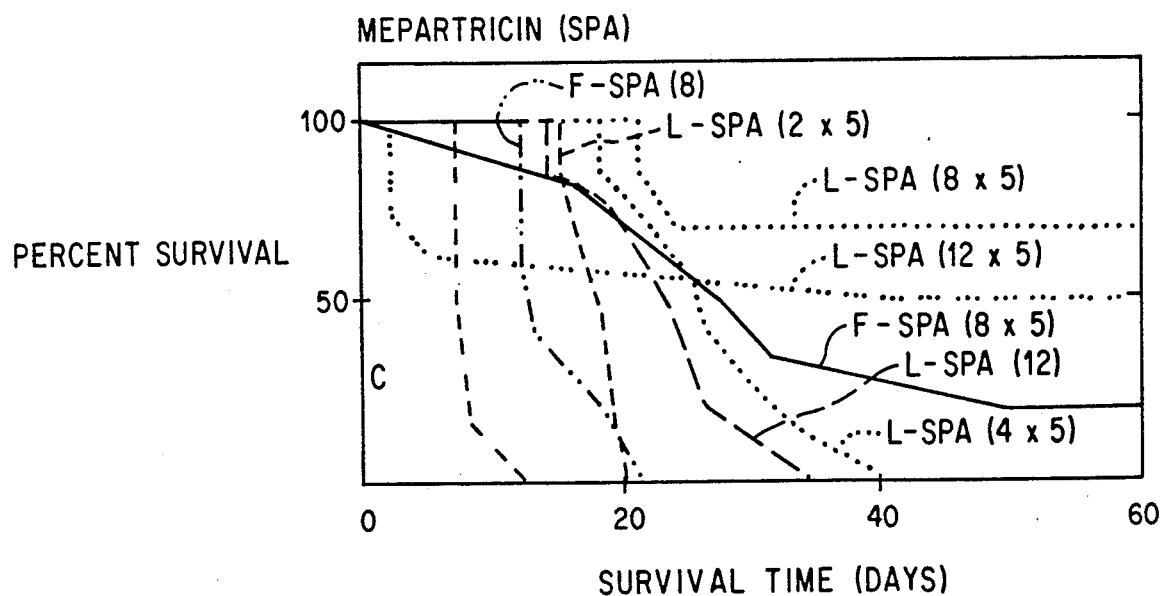
Figure 9C:
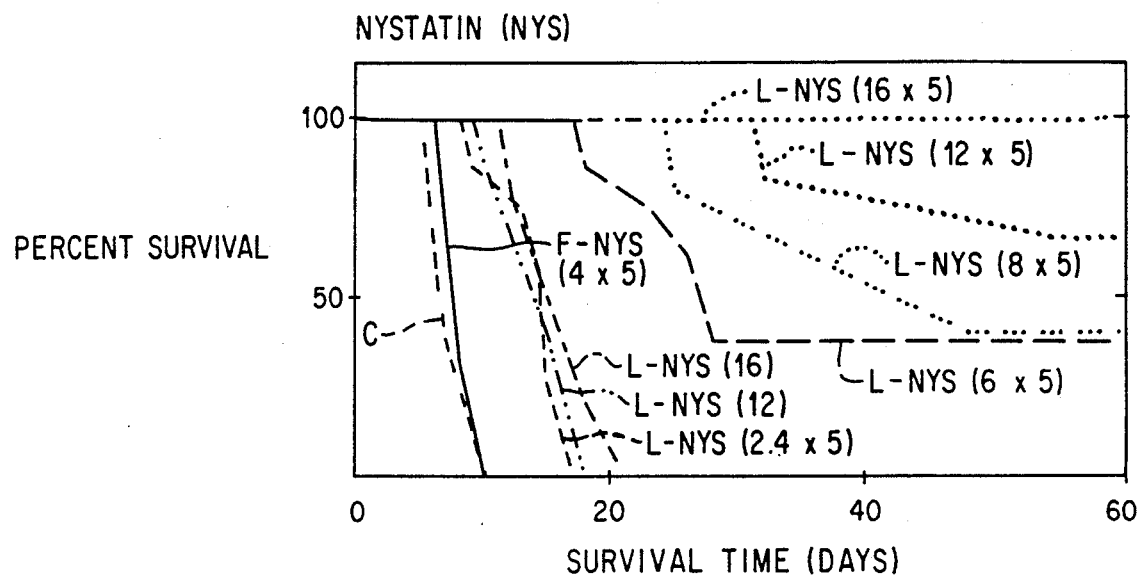
Figure 9D:
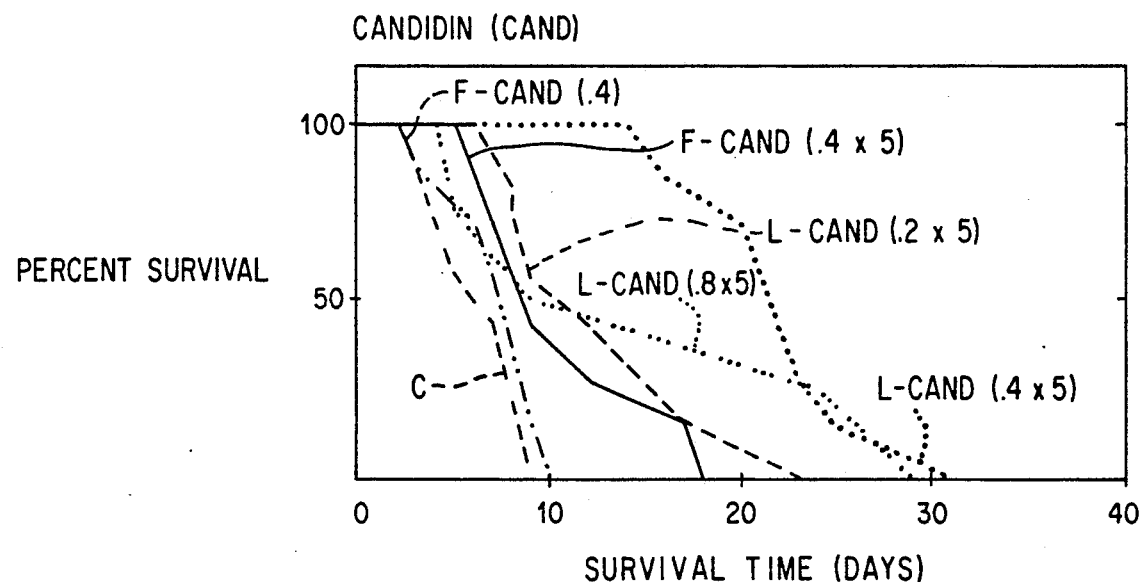
Figure 10A:
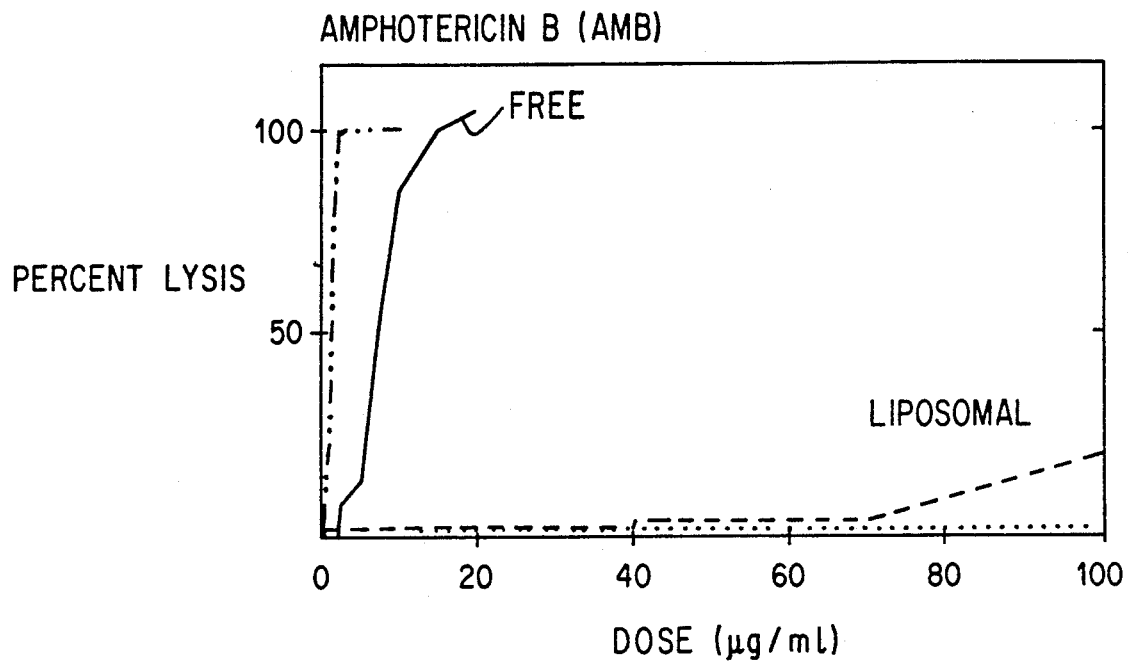
FIG. 10 shows the in vitro toxicity of free-verses liposome-encapsulated large polyenes, including mepartricin.
Figure 10B:
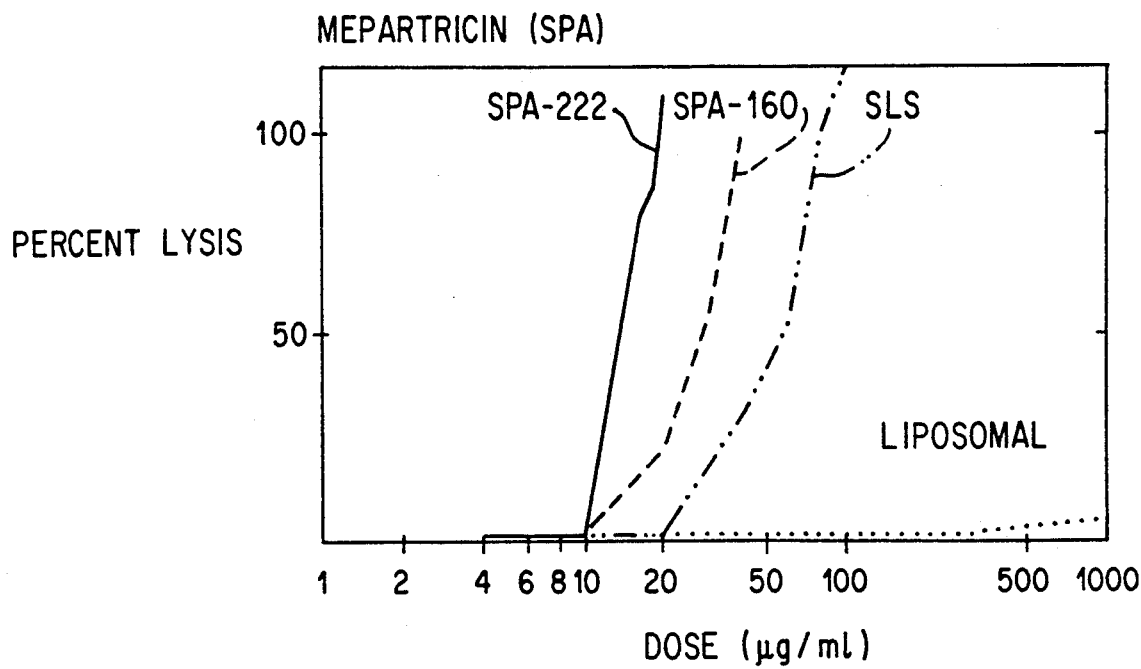
Figure 10C:
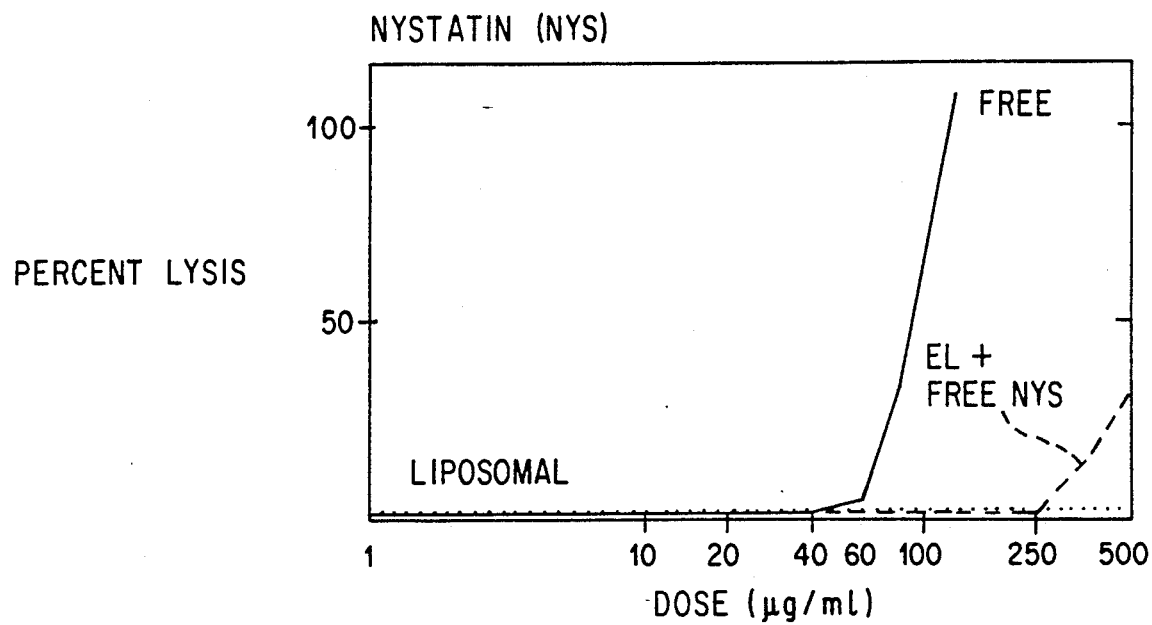
Figure 10D:
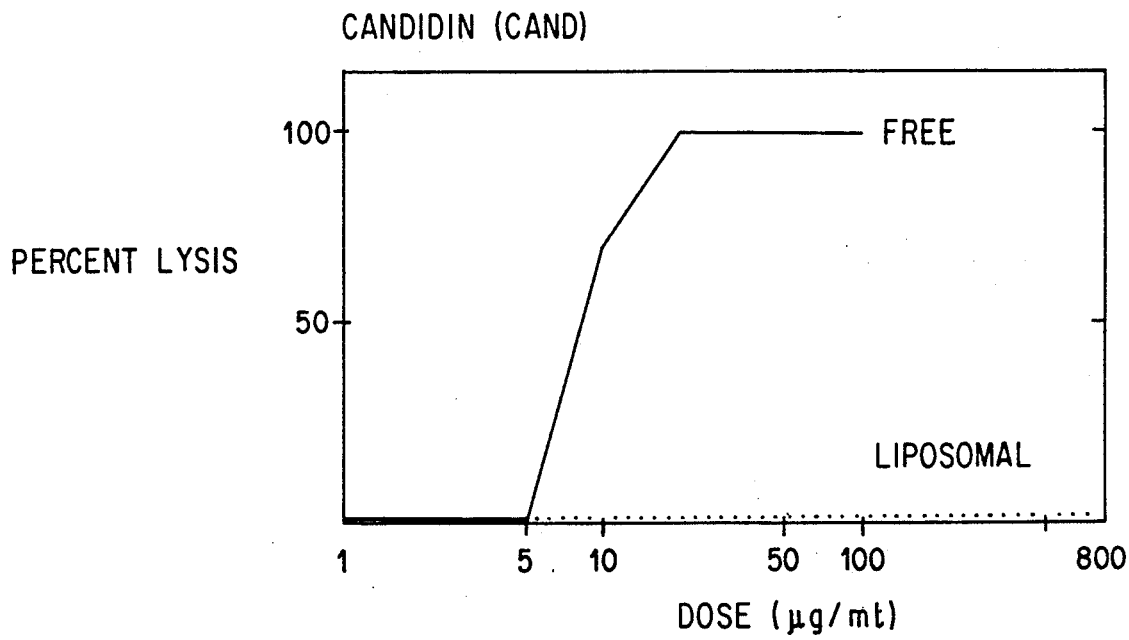
Figure 11A:
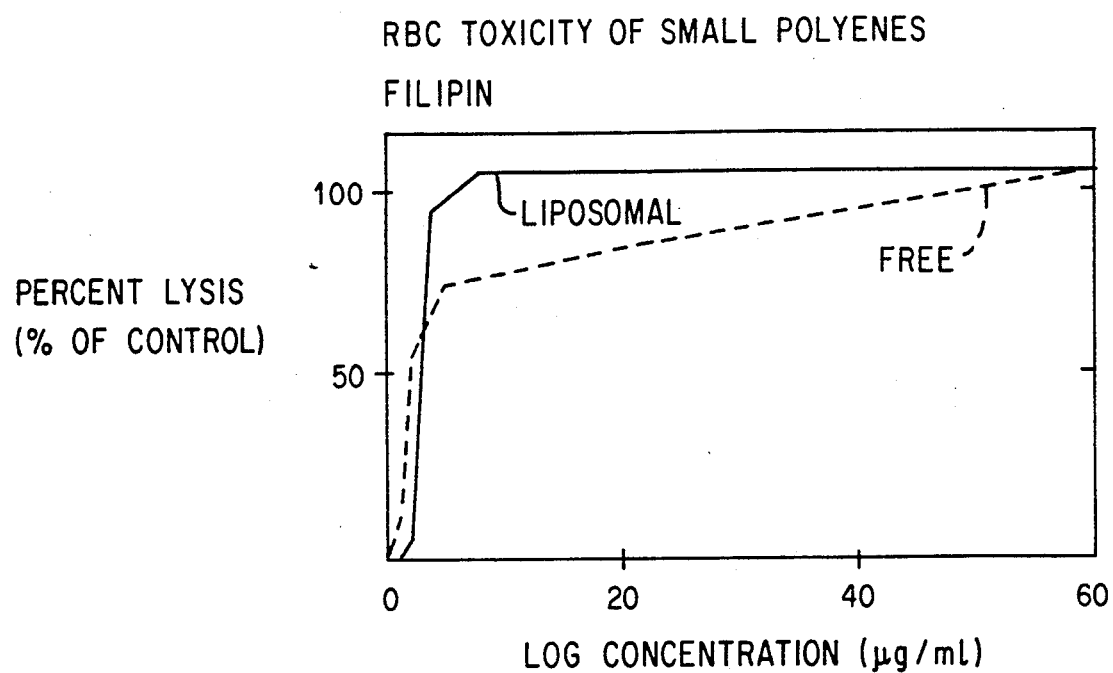
FIG. 11 shows the in vitro RBC toxicity of free-verses liposome-encapsulated small polyenes (e.g., filipin, lagosin and natamycin).
Figure 11B:
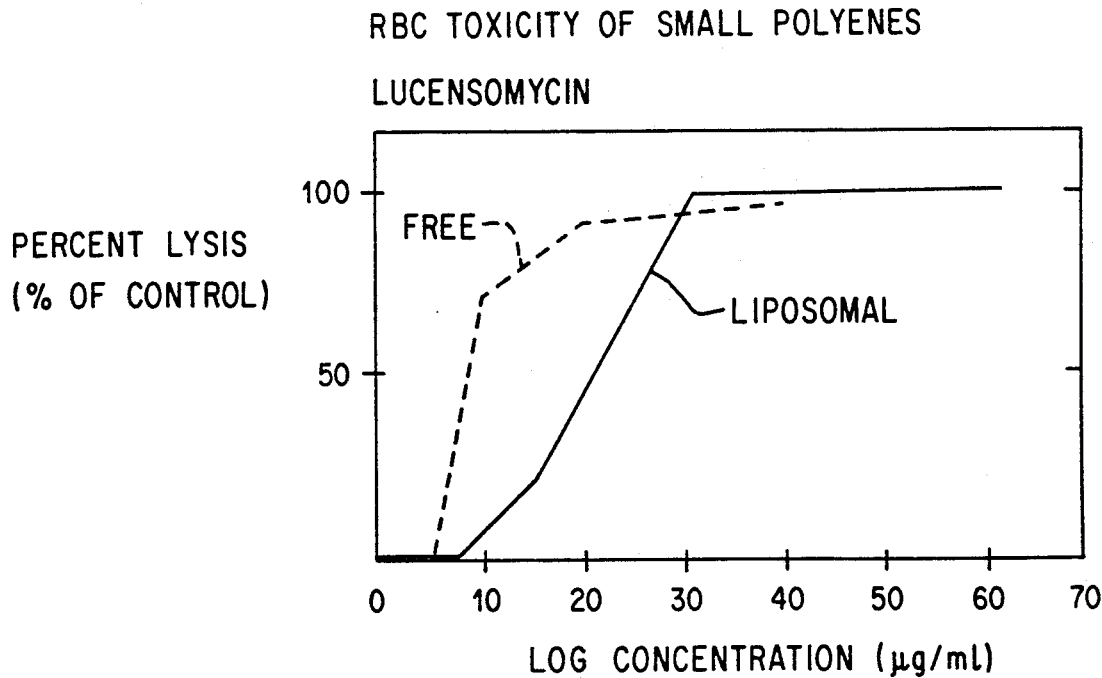
Figure 11C:
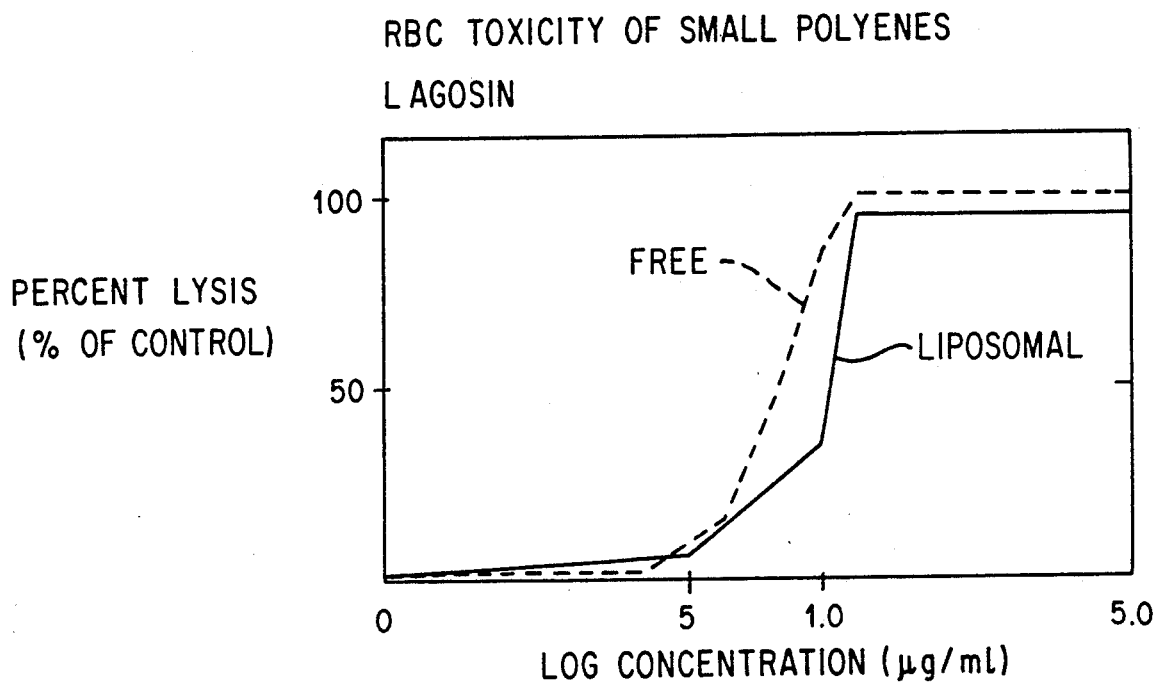
Figure 11D:
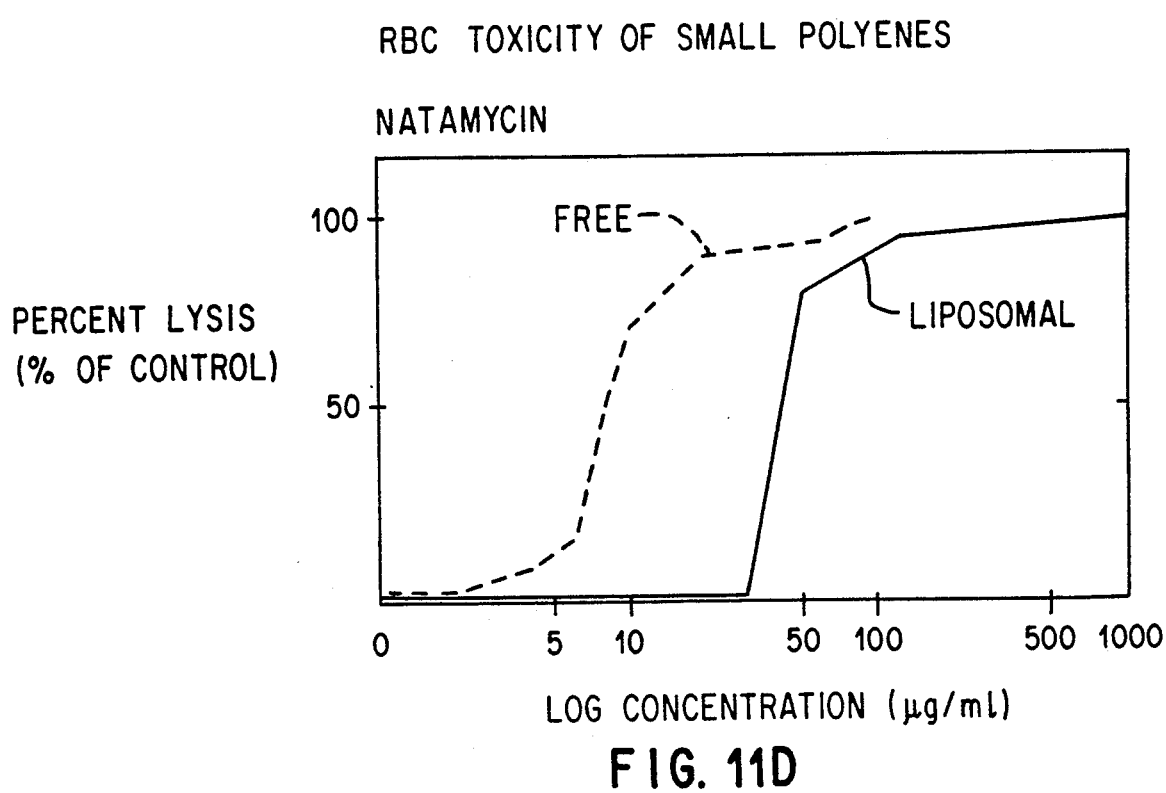

As shown in FIG. 5, free-lucensomycin produced 70% lysis at 10 mg/ml concentration whereas liposomal drug had a substantially less toxic effect at the equivalent concentration. However, a 30 mg/ml concentration of both free-lucensomycin and liposomal-lucensomycin prepared without cholesterol produced approximately 100% lysis.

EXAMPLE 7

In vivo Toxicology of Free-Hamycin and Liposomal-Hamycin

Groups of eight Hale-Stoner mice (6–8 weeks old, body wt=20–25 g; Univ. of TX Science Park, Bastrop, TX) each were injected with various doses of free-hamycin (in 5% DMSO diluted with saline), liposomal-hamycin without cholesterol, and liposomal-hamycin having a gradually increasing percentage of cholesterol. (FIG. 2) The mice were observed for acute, subacute, and chronic toxicity and the survival time of each animal in different groups was noted. After 90 days, the surviving animals were sacrificed and blood and tissue samples were obtained. Blood biohemistry examination included blood urea nitrogen, alkaline phosphatase, and lactic dehydrogenase (LDH). The organs (liver, spleen, lungs and kidneys) were obtained and preserved in 10% formalin. Tissue slices were processed for hematoxylin-eosin and Gomori methenamine silver stains.

The maximal tolerated dose (MTD) of both liposomal-hamycin without cholesterol and free-hamycin was 20 micrograms/mouse. Liposomal-hamycin containing cholesterol, on the other hand, showed a maximum tolerated dose of 62 micrograms/mouse using liposomes containing 60% cholesterol. The MTD increased as the percent of cholesterol increased. No subacute or chronic toxic reactions were observed in the surviving animals. Nor were there any significant changes in the blood biochemistry pattern for the surviving animals.

EXAMPLE 8

Therapy with Single Dose Free-Hamycin for Disseminated Fungal Infection with *Candida albicans*

Figure 4:
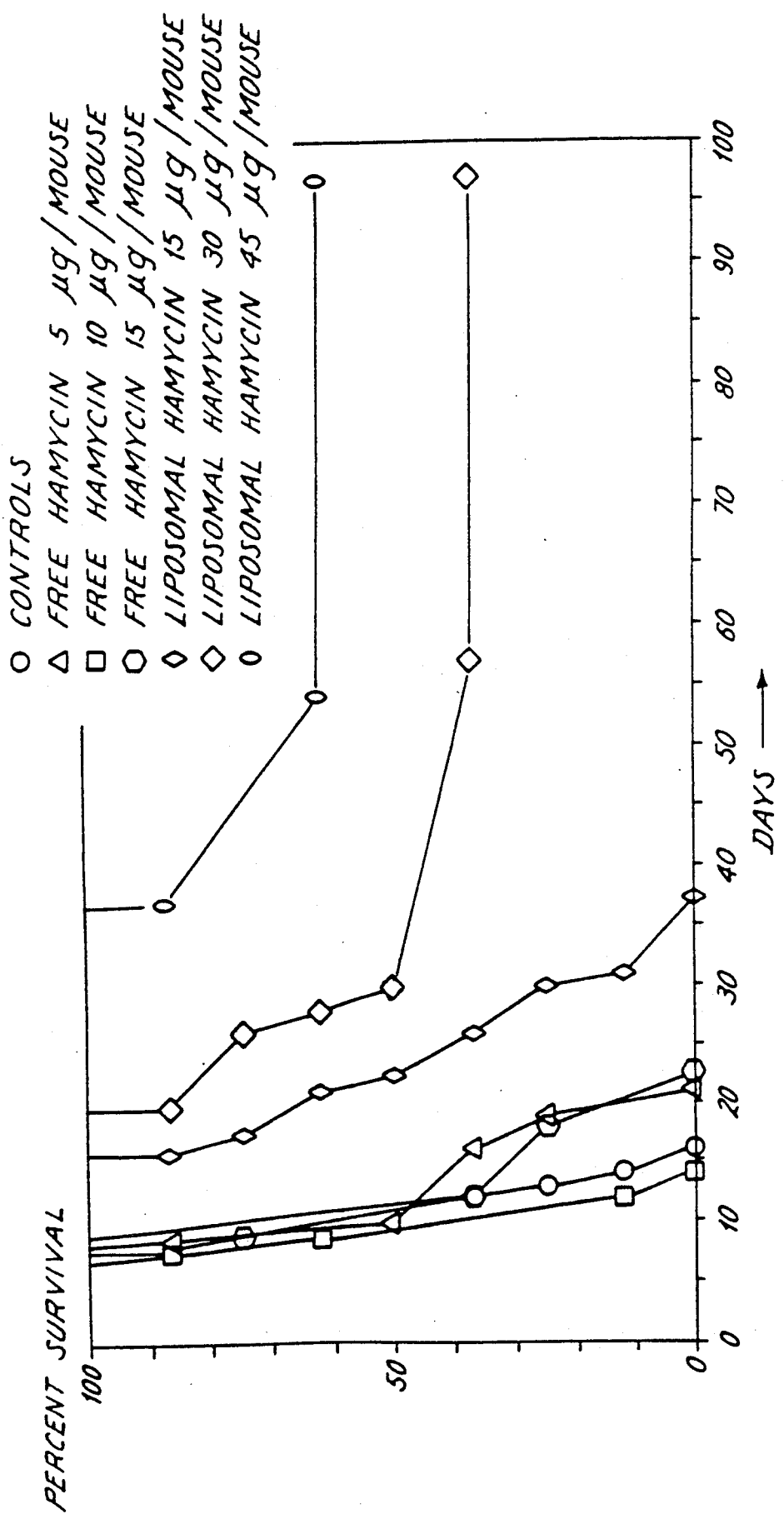
FIG. 4 shows the antifungal affect of free versus liposomal-hamycin in mice. Various doses of hamycin were given to mice and their survival was measured and recorded. Specifically, the doses administered were ( ) controls, ( ) free-hamycin 5 mg/mouse, ( ) free-hamycin 10 mg/mouse, (○) free-hamycin 15 mg/mouse, (△) liposomal-hamycin 15 mg/mouse, (□) liposomal-hamycin 30 mg/mouse, ( ) 45 mg/mouse.

Hale-Stoner mice, six to eight weeks old (body weight, 20–25 g) were purchased from The University of Texas Science Park (Bastrop, TX). The mice (eight per group) were injected with 0.2 ml of *C. albicans* cell suspension containing $7 \times 10^5$ colony-forming units (cfu) via the tail vein. This concentration of cells was consistent in producing a disseminated infection after 48 hr, affecting primarily the liver, spleen, lungs and kidneys. Infected mice were treated with increasing doses of free-hamycin from 5 microgram/mouse (FIG. 4). None of the doses tested improved the survival of infected mice as compared to the control untreated group.

EXAMPLE 9

Therapy with Single Dose Liposomal-Hamycin for Disseminated Fungal Infections with Candida albicans Mice were infected with *C. albicans* as described in Example 7. Groups of eight mice each were injected (iv) with various doses of liposomal-hamycin two days after the injection of *C. albicans*. The survival of the animals in each group was recorded. (FIG. 4).

Differences in survival of mice was observed with all doses of liposomal-hamycin as compared with free-hamycin. Significant improvement in survival was observed in the liposomal-hamycin treated groups when compared with the free-hamycin group. However, all mice were sacrificed at 90 days, regardless of treatment. Results of culture and histopathology showed approximately 50% of animals free from infection.

EXAMPLE 10

Drug, Lipids and Reagents

Lucensomycin (bulk powder) was obtained from CNR (Italy). Chromatographically pure dimyristoyl phosphatidylcholine (DMPC) and dimyristoyl phosphatidylglycerol (DMPG) were purchased from Avanti Polar Lipids (Birmingham, Ala.). Methanol for highperformance liquid chromatography (HPLC), dimethyl sulfoxide (DMSO), and N,N-dimethylformamide (DMFA) were purchased from Fisher Scientific (Fair Lawn, N.J.). Human AB serum was from MA Bioproducts (Walkersville, Md.) Human RBCs were obtained from normal volunteers.

EXAMPLE 11

Liposome Preparation and Standardization

Multilamellar vesicles (MLV) were prepared as described previously (Lopez-Berestein et al., *J. Infect. Dis.*, 120; 278-283 (1984)). Cholesterol, and the phospholipids DMPC:DMPG (7:3), were mixed with increasing amounts of the lucensomycin and the organic solvents evaporated under vacuum using a rotary evaporator. The dried cholesterol-lipid-drug film was suspended in phosphate-buffered saline (PBS) and handshaken, allowing the film to form liposomes. The suspensions were then recovered from the flasks and centrifuged at 20,000 rpm for 1 hr. The pellets were resuspended in PBS and lucensoxycin incorporated in liposomes was determined by absorbance at 303 nm. Similarly, liposomes composed of phospholipids and without cholesterol were also prepared. The following Table 4 shows the characteristic properties of these liposomes.

TABLE 4
LIPOSOME PREPARATION

| Name of the drug | Lucensomycin | | |
|---|---|---|---|
| Batch No. | P.H. 59659 | | |
| Source | CNR, Milano, Italy | | |
| Chemical structure | Polyene | | |
| | Solvent | 1 mg/ml | Maximum |
| Solubility | 1. water/saline | nil | — |
| | 2. Methanol | Partial | 500 ug/ml |
| | 3. DMSO | Yes | 20 mg/ml |
| | 5. DMFA | Yes | 10 mg/ml |
| Quantitation | UV absorption at 303 nm | | |
| Encapsulation efficiency | 1. DMPC:DMPG (7:3) | | 75% |
| Drug/lipid ratio | 1:10 | | |

EXAMPLE 12

Encapsulation Efficiency of Lucensomycin in Liposomes

The encapsulation efficiencies were calculated for different batches of liposomes prepared with a fixed amount of liposome and increasing doses of lucensomycin. The maximum incorporation was 75% obtained at a drug/phospholipid ratio of 1:10.

EXAMPLE 13

In vitro fungal inhibition

The antifungal activity of free- versus liposomal-lucensomycin against *Candida albicans* (Strain 336) was determined in vitro. All strains of yeast were grown overnight at 37° C. on Sabouraud dextrose agar (SDA) plates. All molds were grown at 30° C. on SDA for 3 to 10 days prior to collection of spores. The inoculum was then processed for susceptibility testing as described earlier (Hopfer et al., (1984), *Antimicrob. Agents Chemotherap.*, 25:387-389). A twofold serial dilution method (Shadomy et al., E. H. Lennette, (eds.) Manual of Clinical Microbiology, 3rd ed. American Society for Microbiology, Washington, D.C. , pp. 647-653 (1980)) adapted to microtiter plates was used to determine the minimal inhibitory concentration (MIC) of the drugs. The MIC of free-lucensomycin was compared with that of liposomal-lucensomycin.

The MIC of free-lucensomycin and the MIC for liposomal-hamycin demonstrated high antifungal activity. The antifungal activity was maintained in liposomallucensomycin with or without cholesterol.

EXAMPLE 14

Toxicity of Free-Lucensomycin and Liposomal-Lucensomycin Prepared with Cholesterol to Human RBC's in vitro Lysis of human red blood cells (RBCs) was quantitated by measuring the release of hemoglobin in the supernatants at 540 nm, as described previously (Mehta et al., (1984) *Biochem. Biophys. Acta.*, 770:230-234). Various doses of liposomal-lucensomycin prepared with cholesterol were incubated with various concentrations of fresh washed human RBCs at 37° C. for 45 min. Free-lucensomycin, dissolved in dimethyl formamide (DMFA), was added to the assay at a 3% final solvent concentration. Release of hemoglobin by hypotonic lysis of the same number of human RBCs by water was taken as 100% positive control, while cells treated with PBS were taken as negative controls.

Lucensomycin-liposomes containing 3 mg cholesterol per 10 mg phospholipids (60% by weight) were found to be less toxic than those with no cholesterol or those containing 1 or 2 mg cholesterol. (FIG. 5).

EXAMPLE 15

In vivo Toxicity of Liposomal-Mepartricin with Different Lipid Compositions

The in vivo toxicity of liposomal-mepartricin was evaluated in groups of 8 Hale-Stone mice (6-8 weeks old, body weight =20-25g; University of Texas Science Park, Bastrop, Tex.). Liposomal-mepartricin was prepared following the protocol set forth in Example 2. However, the composition of the liposome was varied in order to determine the optimal formulation to buffer the toxicity of mepartricin. The composition of the liposomes formulated and evaluated in this study are listed in Table 5. Each liposomal-mepartricin preparation was administered to a group of normal and a group of infected mice. These infected mice were injected with 0.2 ml of *C. albicans* according to the protocol set forth in Example 6. Percent survival was also evaluated in days after treatment with liposomal mepartricin. As shown in FIG. 8, it was surprising to note that liposome mepartricin (DMPC:DMPG, 7:3) was more toxic than the free drug. This observation prompted manipulation of the liposome composition to be used. The data on MTD of various liposomal-mepartricin preparations in normal and infected mice is presented in Table 5. Of these, three lipid preparations were found to buffer the toxicity of mepartricin significantly; PC:chol(9:1), DOPC:PE:chol(6:3:1) and DEPC:PE:chol(6:3:1).

The respective MTD's (mg/kg) obtained for the various liposomal-mepartricin indicate the inclusion of cholesterol precludes an immediate toxicity, with the exception of the DEPC:chol (9:1) mepartricin liposome. Of these, particular lipid compositions were found to buffer the toxicity significantly. These were PC:chol (9:1), DOPC:PE:chol (7:3:1) and DEPC:PE:chol (7:3:1). FIGS. 9 and 10 show the survival rate and in vitro toxicity of free versus liposome-encapsulated large polyenes, including mepartricin.

TABLE 5

IN VIVO TOXICITY OF LIPOSOMAL MEPARTRICIN WITH DIFFERENT LIPID COMPOSITIONS

| Lipid composition[b] | Immediate reaction[a] at 8 mg/kg dose | MTD (mg/kg) Normal mice | MTD (mg/kg) Infected mice |
|---|---|---|---|
| DMPC:DMPG (7:3) | Yes | <8.0 | 4.0 |
| DMPC:DMPG:chol (6:3:1) | No | 8.0 | — |
| DMPC alone | Yes | <8.0 | — |
| DMPC:chol (9:1) | No | 12.0 | — |
| EGG PC alone | Yes | <8.0 | — |
| Egg PC:chol (9:1) | No | 20.0 | 12.0 |
| DPPC alone | No | <8.0 | — |
| DPPC:chol (9:1) | No | 8.0 | — |
| DPPC:PE:chol (6.5:2.5:1) | No | 16.0[c] | — |
| DSPC alone | No | <8.0 | — |
| DSPC:chol (9:1) | No | 10.0 | — |
| DSPC:PE:chol (6.5:2.5:1) | No | 20.0 | 10.0 |
| DOPC alone | No | 8.0 | 4.0 |
| DOPC:chol (9:1) | No | 14.0 | — |
| DOPC:PE:chol (6:3:1) | No | 20.0 | 12.0 |
| DEPC alone | Yes | <8.0 | — |
| DEPC:chol (9:1) | Yes | <8.0 | — |
| DEPC:PE:chol (6.5:2.5:1) | No | 14.0 | — |

[a]The animals that had immediate reactions died instantly after the intravenous injection.
[b]DMPC, dimyristoyl phosphatidylcholine; DMPG, dimyristoyl phosphatidylglycerol; EGG PC, egg phosphatidylcholine; DPPC, dipalmitoyl phosphatidylcholine; PE, phospholatidyl ethanolamine; DSPC, distearoyl phosphatidylcholine; DOPC, dideoyl phosphatidyl choline; DEPC, dielaidyl phosphatidyl choline; chol, cholesterol.
[c]Mice died after 24 hours.

EXAMPLE 16

The antifungal activity of free-verses liposomal-small polyenes was determined in vivo. These small polyenes included filipin, lagosin and natamycin.

The in vivo toxicity of liposomal small polyenes was evaluated in groups of 8 Hale-Stone mice (6-8 weeks old, body weight =20-25g; University of Texas Science Park, Bastrop, Tex.). Liposomal polyenes were prepared following the protocol set forth in Example 2. Each liposomal-small polyene formulated and evaluated in this study, listed in table 6, was administered to a group of normal and a group of infected mice. These infected mice were prepared by injection with 0.2 ml. of *C. albicans* according to the protocol set forth in Example 6.

The data on MIC of various liposomal-mepartricin preparations in normal and infected mice is presented for each of the small polyenes (filipin, lagasin natamysin and nystatin) and large polyenes in Table 6.

TABLE 6

ANTIFUNGAL ACTIVITY OF FREE VERSUS LIPOSOMAL POLYENES

| Polyene | MIC (ug/ml) Free | MIC (ug/ml) Liposomal |
|---|---|---|
| Small | | |
| Filipin | 8.0–16.0 | 16.0 |
| Lagosin | 4.0 | 3.0 |
| Natamycin | 4.0 | 8.0 |
| Nystatin | 1.0 | 1.0 |
| Large | | |
| Amphotericin B | 0.4 | 0.4 |
| Candidin | 5.0 | 5.5 |
| Mepartricin | 2.0–4.0 | 2.0 |

Of these, it appears the MIC of liposomal-natamycin is significantly increased from that of its free-form (i.e., free=4.0 MIC vs. liposomal=8.0 MIC). The MIC of lagosin was reduced 25% (4.0 MIC−3.0 MIC) by encapsulation.

EXAMPLE 16

Toxicity of Free-Small Polyenes and Liposomal-small polVenes to Human RBC's in vitro Lysis of human red blood cells (RBCs) was quantitated by measuring the release of hemoglobin in the supernatants at 540 nm, as described previously (Mehta, et al. (1984) *Biochem. Biophys. Acta*, 770:230-234). Various doses of the liposomal-small polyenes described in Example-16 were prepared and incubated with various concentrations of fresh washed human RBC's at 37° C. for 45 min. Release of hemoglobin by hypotonic lysis of the same number of human RBCs by water was taken as 100% positive control, while cells with PBS were taken as negative controls.

As shown in FIG. 11, the incorporation of small polyenes in liposomes did not significantly reduce RBC toxicity. The toxicity pattern of filipin and lagosin did not change with liposome encapsulation, whereas liposome encapsulation of natamycin provided some protection of lower doses (5–40 ug/ml dose)

Changes may be made in the elements and methods described herein or in the steps or the sequence of steps of the method described herein without departing from the concept and scope of the invention as defined in the following claims.

What is claimed is:

1. A liposomal agent for treating disseminated fungal infection in an animal, said agent comprising;
    (a) hamycin,
    (b) at least 10% of a sterol by weight, and
    (c) at least 25% lipids by weight.

2. The liposomal agent of claim 1 wherein the polyene macrolide antifungal compound comprises from about 0.1 to about 10% by weight of the liposomal agent.

3. The liposomal agent of claim 1 wherein the lipids are one or more of phosphomonoglyceride, phosphatidic acid and sphingolipid.

4. The liposomal agent of claim 1 wherein the lipids are one or more of phosphatidylcholine, phosphatidylserine, phosphatidylglycerol, sphingomyelin and phosphatidic acid.

5. The liposomal agent of claim 1 wherein the lipids are one or more of the group consisting of: dimyristoyl phosphatidylcholine, dimyristoyl phosphatidylglycerol, phosphatidylcholine, phosphatidylglycerol, dideoyl phosphatidylcholine, dielaidyl phosphatidylcholine, and phosphatidylethanolamine.

6. The liposomal agent of claim 1 wherein the lipids include dimyristoyl phosphatidylcholine and dimyristoyl phosphatidylglycerol.

7. The liposomal agent of claim 11 wherein the weight ratio of dimyristoyl phosphatidlycholine: dimyristoyl phosphatidylglycerol is between about 1:10 and about 10:1.

8. The liposomal agent of claim 1 wherein the lipids are comprised of dimyristoyl phosphatidylcholine and dimyristoyl phosphatidylglycerol in a weight ratio of about 7:3.

9. The liposomal agent of claim 1 defined further as being a stable multilamellar vesicle.

10. The liposomal agent of claim 1 wherein the sterol is cholesterol.

11. The liposomal agent of claim 1 wherein the sterol is ergosterol.

12. The liposomal agent of claim 10 wherein the sterol is cholesterol and comprises from about 10 to about 75% by weight of the liposomal agent.

13. The liposomal agent of claim 10 wherein the sterol is cholesterol and comprises about 60% by weight of the liposomal agent.

14. The method for treatign disseminated fungal infection in an animal comprising administering to an animal a fungicidally effective amount of the liposomal agent of claim 1.

15. The method of claim 14 wherein the mode of administering the liposomal agent is oral, topical or parenteral.

16. The method of claim 14 wherein the mode of administering the liposomal agent is parenteral.

17. The method of claim 14 wherein the animal is a human.

18. The method of claim 14 wherein the fungicidally effective amount is between about 0.1 mg /kg body weight and about 80 mg/kg body weight.

19. The method of claim 14 wherein the mode of administering the liposomal agent is intravenous, intraarterial, subcutaneous, intramuscular, intralymphatic, intraperitoneal or intrapleural.

* * * * *

UNITED STATES PATENT AND TRADEMARK OFFICE
CERTIFICATE OF CORRECTION

PATENT NO. : 5,032,404
DATED : July 16, 1991
INVENTOR(S) : Gabriel Lopez- Berestein, et al It is certified that error appears in the above-identified patent and that said Letters Patent is hereby corrected as shown below:

In the title of the patent, "LIPSOME" should read --LIPOSOME--. See the title page of the application.

At column 2, line 31, "bloo    should read --blood, causing

At column 6, line 42, "(  ) PL" should read --(○) PL--.

At column 6, line 43, "(  ) PL:CHOL (cholesterol) (5%)" should read --(△) PL:CHOL (cholesterol) (5%)--.

At column 6, lines 43-44, "(  ) PL:CHOL (10%)" should read --(□) PL:CHOL (10%)--.

At column 6, line 44, "(  ) PL:CHOL (20%)" should read --(◊) PL:CHOL (20%)--.

At column 6, line 44, "(△) PL:CHOL (30%)" should read

UNITED STATES PATENT AND TRADEMARK OFFICE
CERTIFICATE OF CORRECTION

PATENT NO. : 5,032,404
DATED : July 16, 1991
INVENTOR(S) : Gabriel Lopez-Berestein, et al It is certified that error appears in the above-identified patent and that said Letters Patent is hereby corrected as shown below:

--(◊) PL:CHOL (30%)--.

At column 6, line 45, "(□) PL:CHOL (40%)" should read --(◊) PL:CHOL (40%)--.

At column 6, line 45, "( ) PL:CHOL (60%)" should read --(○) PL:CHOL (60%)--.
application.

At column 6, line 50, "( ) controls" should read --(○) controls--.

At column 6, line 50, "( ) free-hamycin 5 mg/mouse" should read --(△) free-hamycin 5 mg/mouse--.

UNITED STATES PATENT AND TRADEMARK OFFICE
CERTIFICATE OF CORRECTION

PATENT NO. : 5,032,404
DATED : July 16, 1991
INVENTOR(S) : Gabriel Lopez-Berestein, et al It is certified that error appears in the above-identified patent and that said Letters Patent is hereby corrected as shown below:

At column 6, lines 50-51, "( ) free-hamycin 10 mg/mouse" should read --(□) free-hamycin 10 mg/mouse--.

At column 6, lines 51-52, "(○) free-hamycin 15 mg/mouse" should read --(◊) free-hamycin 15 mg/mouse--.

At column 6, line 52, "(△) liposomal-hamycin 15 mg/mouse" should read --(◊) liposomal-hamycin 15 mg/mouse--.

At column 6, lines 52-53, "(□) liposomal-hamycin 30 mg/mouse" should read --(◊) liposomal-hamycin 30 mg/mouse--.

At column 6, line 53, "( ) 45 mg/mouse" should read --(○) liposomal-hamycin 45 mg/mouse--.

At column 6, line 57, "( ) free-lucensomycin" should read

UNITED STATES PATENT AND TRADEMARK OFFICE
CERTIFICATE OF CORRECTION

PATENT NO. : 5,032,404
DATED : July 16, 1991
INVENTOR(S) : Gabriel Lopez-Berestein, et al It is certified that error appears in the above-identified patent and that said Letters Patent is hereby corrected as shown below:

--(☐) free-lucensomycin--.

At column 6, lines 57-58, "( ) liposomal-lucensomycin" should read --(○) liposomal-lucensomycin--.
page 14, line 33 of the application.

At column 6, lines 62-63, "( ) cholesterol concentration 20%" should read --(○) cholesterol concentration 20%--.

At column 6, line 63, "( ) cholesterol concentration (40%)" should read --(☐) cholesterol concentration (40%)--.

At column 6, lines 63-64, "( ) cholesterol concentration 60%" should read --(△) cholesterol concentration 60%--.

At column 7, line 43, "1968" should read --1986--.

UNITED STATES PATENT AND TRADEMARK OFFICE
CERTIFICATE OF CORRECTION

PATENT NO. : 5,032,404

DATED : July 16, 1991

INVENTOR(S) : Gabriel Lopez-Berestein, et al

It is certified that error appears in the above-identified patent and that said Letters Patent is hereby corrected as shown below:

At column 11, line 27, "dilutron" should read --dilution--.

At column 11, line 43, "LiposomalHamycin" should read --Liposomal Hamycin--.

At column 11, line 50, "iresh" should read --fresh--.

At column 11, line 59, "haxycin" should read --hamycin--.

At page 13, line 39, "(1984})" should read --(1984))--.

At column 16, line 30, "polVenes" should read --polyenes--.

At column 18, line 7 (the first line of claim 14), "treatign" should read --treating--.

UNITED STATES PATENT AND TRADEMARK OFFICE
CERTIFICATE OF CORRECTION

PATENT NO. : 5,032,404

DATED : July 16, 1991

INVENTOR(S) : Gabriel Lopez-Berestein, et al

It is certified that error appears in the above-identified patent and that said Letters Patent is hereby corrected as shown below:

At column 16, line 30, "polyVenes" should read --polyenes--.

At column 18, line 7 (the first line of claim 14), "treatign" should read --treating--.

Signed and Sealed this

Ninth Day of March, 1993

Attest:

STEPHEN G. KUNIN

Attesting Officer     Acting Commissioner of Patents and Trademarks